(12) United States Patent
Keertikumar

(10) Patent No.: US 10,849,578 B2
(45) Date of Patent: Dec. 1, 2020

(54) MEDICAL DEVICE

(71) Applicant: Samsung Electronics Co., Ltd., Gyeonggi-do (KR)

(72) Inventor: Davevikram Keertikumar, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 252 days.

(21) Appl. No.: 15/667,555

(22) Filed: Aug. 2, 2017

(65) Prior Publication Data
US 2018/0184991 A1 Jul. 5, 2018

(30) Foreign Application Priority Data
Dec. 29, 2016 (KR) .................. 10-2016-0182916

(51) Int. Cl.
*A61B 6/00* (2006.01)
*A61B 6/03* (2006.01)
*A61B 6/04* (2006.01)

(52) U.S. Cl.
CPC ............... *A61B 6/4405* (2013.01); *A61B 6/03* (2013.01); *A61B 6/032* (2013.01); *A61B 6/035* (2013.01); *A61B 6/4435* (2013.01); *A61B 6/4452* (2013.01); *A61B 6/0442* (2013.01); *A61B 6/4447* (2013.01); *A61B 6/5247* (2013.01)

(58) Field of Classification Search
CPC ........ A61B 6/032; A61B 6/035; A61B 6/4405
USPC ......................................................... 378/197
See application file for complete search history.

(56) References Cited

U.S. PATENT DOCUMENTS

| 4,829,549 | A | * | 5/1989 | Vogel .................... A61B 6/505 378/146 |
| 5,448,607 | A | | 9/1995 | McKenna |
| 5,638,419 | A | | 6/1997 | Ingwersen |
| 5,848,126 | A | | 12/1998 | Fujita et al. |
| RE36,099 | E | | 2/1999 | Gordon |
| 6,212,251 | B1 | | 4/2001 | Tomura et al. |
| 6,408,045 | B1 | * | 6/2002 | Matsui ............... G03F 7/70716 378/34 |
| 6,959,068 | B1 | | 10/2005 | Sommer |
| 8,057,097 | B1 | | 11/2011 | Tybinkowski et al. |

(Continued)

FOREIGN PATENT DOCUMENTS

| DE | 10-2012-201527 A1 | 5/2013 |
| DE | 10-2014-213204 A1 | 1/2016 |

OTHER PUBLICATIONS

Communication from a foreign patent office in a counterpart foreign application, "European Patent Office, European Search Report," Application No. EP 17195600.6, dated Mar. 28, 2018, 8 pages.

(Continued)

*Primary Examiner* — David P Porta
*Assistant Examiner* — Abra S Fein

(57) ABSTRACT

A medical device for photographing an object includes an improved moveable structure. The medical device includes a gantry, a guide rail configured to guide a movement of the gantry, a belt configured to be pulled out of the gantry to guide the movement of the gantry together with the guide rail and a moving member configured to enable the gantry to move. The moving member also is configured to be movable along the guide rail.

20 Claims, 23 Drawing Sheets

(56) References Cited

U.S. PATENT DOCUMENTS

| | | | |
|---|---|---|---|
| 2004/0206880 A1* | 10/2004 | Henley | A61B 6/035 248/675 |
| 2010/0232577 A1 | 9/2010 | Tybinkowski et al. | |
| 2011/0222667 A1 | 9/2011 | Gregerson et al. | |
| 2011/0315884 A1* | 12/2011 | Worstell | A61B 6/037 250/362 |
| 2014/0037071 A1 | 2/2014 | Foerner et al. | |
| 2016/0066871 A1 | 3/2016 | Tybinkowski et al. | |
| 2017/0265820 A1* | 9/2017 | Atria | A61B 6/032 |
| 2018/0177473 A1* | 6/2018 | Gregerson | A61B 6/00 |

OTHER PUBLICATIONS

European Patent Office, "Communication pursuant to Article 94(3) EPC," Application No. EP17195600.6, dated Dec. 10, 2018, 3 pages.

\* cited by examiner

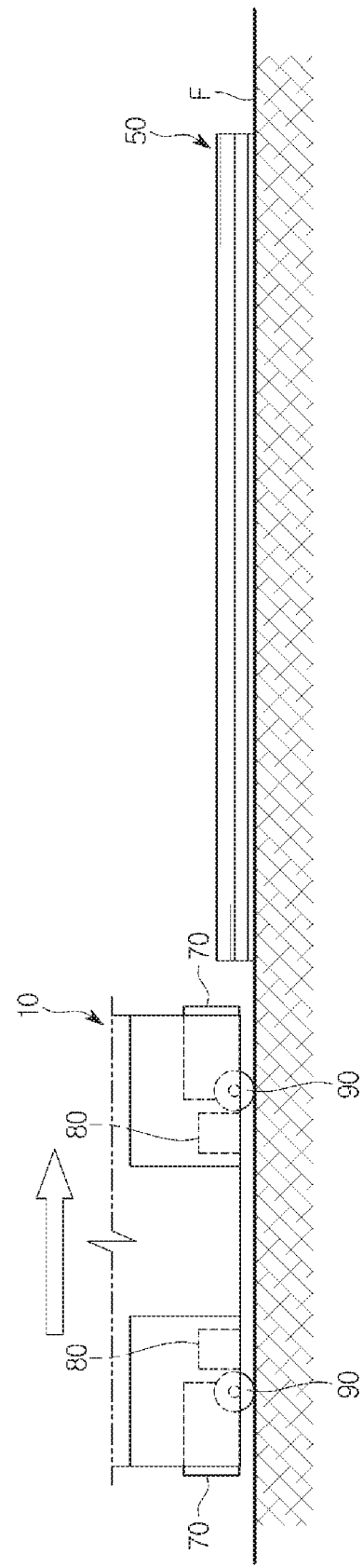

MEDICAL DEVICE

CROSS-REFERENCE TO RELATED APPLICATION

The present application is related to and claims benefit of Korean Patent Application No. 10-2016-0182916, filed on Dec. 29, 2016, the disclosure of which is incorporated herein by reference in its entirety.

TECHNICAL FIELD

The present disclosure relates to a medical device, and more particularly, to a medical device with an improved structure to be movable.

BACKGROUND

An X-ray imaging device is a device that irradiates X-rays on an object and analyzes the X-rays passed through the object to show the internal structure of the object. Since different internal materials consisting of an object have different X-ray transmittances, the internal structure of an object can be visualized based on attenuation coefficients obtained by digitizing X-ray transmittances.

The X-ray imaging device can be classified into a simple X-ray imaging device that transmits X-rays in one direction and a Computed Tomography (CT) device that transmits X-rays in different directions and reconstructs an image with a computer. The CT device is also called a computer tomography apparatus or a computerized tomography apparatus.

Recently, a mobile CT device designed to be movable has attracted attention. The mobile CT device is a device designed to photograph the state of an object in real time. Therefore, when the mobile CT device is used, it is possible to photograph an object during an operation, and to freely move the mobile CT device in an operating room.

The straightness of a path through which the mobile CT device moves may be one of important factors for determining the quality of an image photographed by the mobile CT device. For example, when the floor is uneven, the mobile CT device may move along a path that is different from a target path in a process of photographing an object, and in this case, it is difficult to obtain an accurate image of the object.

SUMMARY

To address the above-discussed deficiencies, it is a primary object to provide a medical device with an improved structure to have mobility and to obtain high-quality images.

The present disclosure also provides a medical device with an improved structure to obtain high-quality images regardless of the condition of a movement path.

The present disclosure also provides a medical device with an improved structure to improve ease of use and to have mobility.

In accordance with one aspect of the present disclosure, a medical device includes a gantry, a guide rail installed to guide a movement of the gantry when the gantry is moved, a belt installed in the gantry, and configured to be pulled out of the gantry to guide the movement of the gantry together with the guide rail and a moving member installed in the gantry to allow the gantry to move, and configured to be movable along the guide rail.

The belt is pulled out of the gantry to be parallel to the guide rail.

In accordance with one aspect of the present disclosure, the medical device further includes a belt holder coupled to one end of the belt to facilitate withdrawal of the belt, and detachably mounted to the gantry.

The belt holder includes a guide rail mounting portion to which the guide rail is detachably coupled.

The belt holder includes a belt holder body and a belt winder rotatably installed inside the belt holder body so that the belt is wound.

The belt holder further includes a belt winder driving unit installed inside the belt holder body to rotate the belt winder using an elastic force.

The belt winder driving unit includes an elastic member capable of being elastically deformed, and the belt pulled out from the gantry is rewound to the belt winder by resilience of the elastic member.

The belt holder further includes a belt clamp mounted on one side of the belt holder body facing the gantry so as to guide a movement of the belt.

The moving member includes at least one chain.

The moving member includes a slider movably coupled to the guide rail.

In accordance with one aspect of the present disclosure, the medical device further includes a caster mounted on the gantry, and configured to protrude from the gantry to allow the gantry to move.

The moving member and the caster selectively allow the gantry to move.

In accordance with one aspect of the present disclosure, the medical device further includes a moving member driving unit provided inside the gantry to supply power to the moving member and a first pulley unit installed adjacent to the moving member driving unit, and configured to guide a movement of the belt inside the gantry, the first pulley unit including a plurality of idler pulleys and a drive pulley positioned above the plurality of idler pulleys in a height direction of the gantry.

In accordance with one aspect of the present disclosure, the medical device further includes a movement preventing unit provided inside the gantry, and configured to prevent the moving member from moving and a second pulley unit installed adjacent to the movement preventing unit, and configured to guide a movement of the belt inside the gantry. The second pulley unit includes a plurality of idler pulleys and a drive pulley positioned above the plurality of idler pulleys in a height direction of the gantry.

In accordance with one aspect of the present disclosure, a medical device includes a gantry configured to be capable of photographing an object, a guide rail installed to guide a movement of the gantry when the object is photographed, a moving member installed in the gantry, and configured to be movable along the guide rail when the object is photographed and a caster installed in the gantry, and configured to be involved in a movement of the gantry when the object is not photographed.

The caster is installed to protrude from the gantry when the object is not photographed.

In accordance with one aspect of the present disclosure, the medical device further includes a belt installed in the gantry, and configured to be capable of being pulled out of the gantry to guide the movement of the gantry together with the guide rail when the object is photographed.

The belt is positioned between the guide rail and the caster to be adjacent to the guide rail.

In certain embodiments, the belt includes a toothed belt.

In accordance with one aspect of the present disclosure, a medical device includes a gantry having a bore into which an object to be photographed is inserted, a guide rail installed when the gantry is moved, and configured to guide a movement of the gantry, a belt installed in the gantry, and configured to be pulled out in an extending direction of the guide rail and a moving member installed in the gantry, and configured to be movable along the guide rail.

In accordance with one aspect of the present disclosure, a medical device includes a gantry, a moving platform disposed below the gantry, and configured to provide mobility to the gantry and a guide rail installed on the moving platform, and configured to guide a movement of the gantry. The moving platform includes a platform body on whose bottom face a plurality of casters are installed and a platform leg rotatably coupled to the platform body.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases. The terms "front", "rear", "upper", "lower", "top", and "bottom" as herein used are defined with respect to the drawings, but the terms may not restrict the shape and position of the respective components.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 11A, 11B and 11C are views illustrating a movement process of a gantry in a medical device according to an embodiment of the present disclosure;

DETAILED DESCRIPTION

FIGS. 1 through 18B, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

A medical device according to the present disclosure is an apparatus for photographing an object to obtain information about living tissues of the object. The medical device according to embodiments of the present disclosure includes an X-ray imaging apparatus for acquiring images of the inside of an object using X-rays, and a magnetic resonance imaging apparatus for acquiring images of the inside of an object using a magnetic resonance phenomenon. Herein, the X-ray imaging apparatus can be classified into a general X-ray imaging apparatus, a dental X-ray imaging apparatus, mammography for photographing breasts, the like, depending on objects to be photographed. The X-ray imaging apparatus can be classified into a general X-ray imaging apparatus for photographing an object at a photographing angle, and a tomography apparatus for photographing an object at different photographing angles and then combining a plurality of images into one image, depending on photographing angles. However, the kind of the medical device according to the present disclosure is not limited to the above examples, and the medical device can be any apparatus capable of acquiring information about an object by photographing the object. Hereinafter, a Computed Tomography (CT) apparatus will be described as an example of the medical device according to the present disclosure.

The object may be a human's or animal's living body, however, the object is not limited to these. That is, the object can be anything having an inside structure can be imaged by the medical device according to the present disclosure. Hereinafter, a human body will be described as an example of the object.

Figure 1:
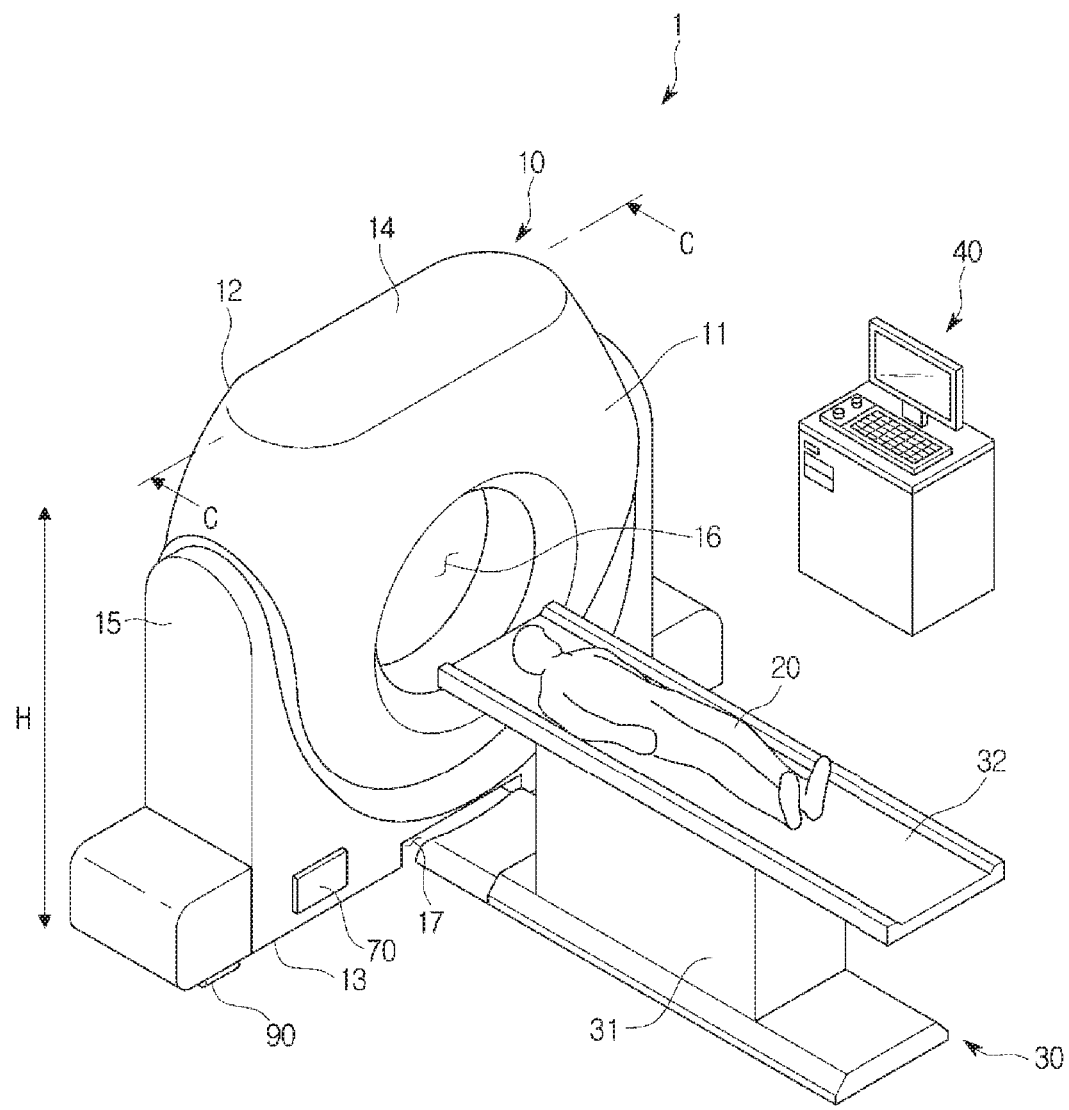
FIG. 1 is a view showing the whole configuration of a medical device according to an embodiment of the present disclosure.

FIG. 1 is a view showing the whole configuration of a medical device according to an embodiment of the present disclosure. In FIG. 1, a reference numeral "70" refers to a belt holder, and a reference numeral "90" refers to a caster. Details about the belt holder and the caster will be described later.

In the example shown in FIG. 1, a medical device 1 includes a gantry 10. The gantry 10 includes an X-ray source to generate X-rays and radiate them to an object 20, and an X-ray detector to detect the X-ray transmitted through the object 20 and to acquire X-ray data.

The gantry 10 includes a front face 11 facing the object 20, a rear face 12 corresponding to the front face 11, a bottom face 13 facing a surface (hereinafter, will be referred to as a floor) on which the gantry 10 moves, a top face 14 corresponding to the bottom face 13, and a side face 15 connecting the front face 11, the rear face 12, the bottom face 13 and the top face 14.

The gantry 10 further includes a bore 16. The object 20 can be inserted into the bore 16. The object 20 can be photographed when the object 20 is inserted into the bore 16.

The gantry 10 can be movable.

Details about the gantry 10 will be described herein below.

The medical device 1 further includes a table 30 on which the object 20 is placed. The table 30 includes a fixed portion 31 and a cradle 32. The cradle 32 can be positioned on the fixed portion 31. More specifically, the cradle 32 can be slidably positioned on the fixed portion 31. The cradle 32 can be inserted into the bore 16 together with the object 20. The cradle 32 can be made of a material through which X-rays can pass so that the object 20 positioned on the cradle 32 can be 3-dimensionally (3-D) photographed. The type of the table 30 is not limited to that which is depicted and described and can be any suitable structure capable of having the object 20 placed thereon. For example, the table 30 can include an operating table, a fixed table, a moving table, and the like.

In certain embodiments, the table 30 can be separated from the gantry 10.

The medical device 1 further includes a workstation 40. The workstation 40 displays images of the object 20 and receives control commands for overall operations of the medical device 1 from a user.

Figure 2:
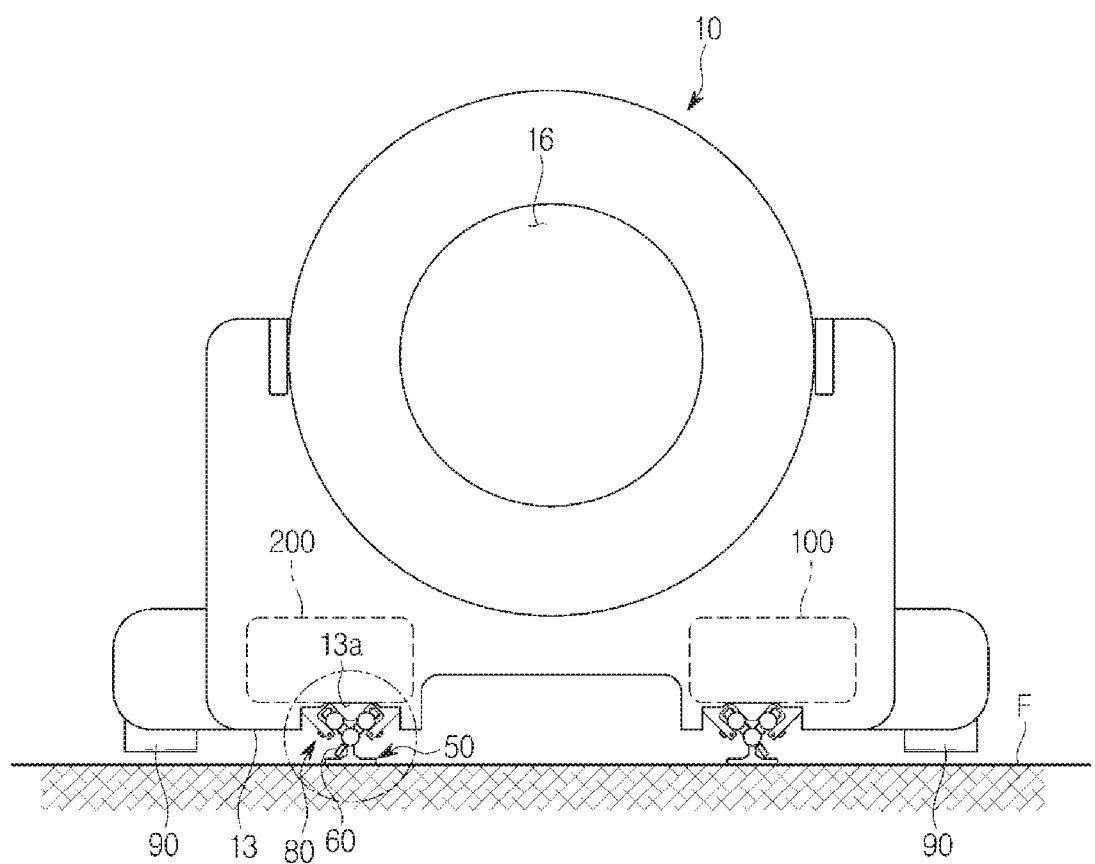
FIG. 2 is a cross-sectional view of a gantry cut along line C-C' of FIG. 1.
Figure 3:
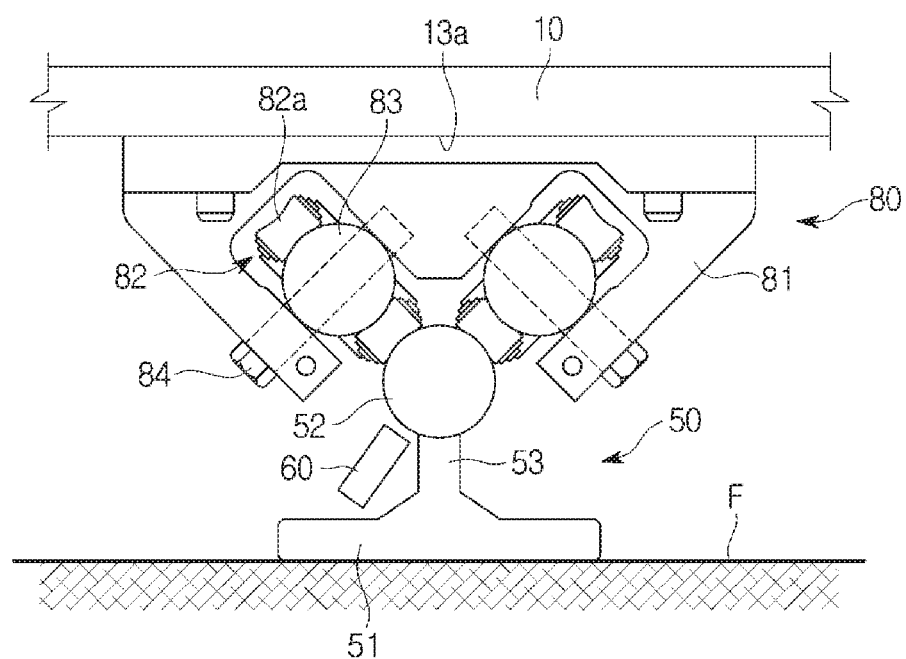
FIG. 3 is an enlarged view illustrating a part of FIG. 2 to which a mobility implementation structure of a gantry according to a first embodiment is applied.

FIG. 2 is a cross-sectional view of a gantry cut along line C-C' of FIG. 1 and FIG. 3 is an enlarged view illustrating a part of FIG. 2 to which a mobility implementation structure of a gantry according to a first embodiment is applied. In the examples shown in FIGS. 2 and 3, "F" refers to the floor.

As shown in FIGS. 2 and 3, the medical device 1 further includes a guide rail 50. The guide rail 50 is installed to support movement of the gantry 10 so as to guide a movement of the gantry 10.

The guide rail 50 can be selectively installed on the floor as required. More specifically, the guide rail 50 can be selectively installed depending on the condition of the floor. The condition of the floor may be one of important factors for determining the quality of images photographed by the medical device 1. That is, when the object is photographed while the gantry 10 moves on an uneven floor, the gantry 10 may move in a path that is different from a target path during photographing. Therefore, it is difficult to precisely or accurately photograph the object 20, and as a result, it is difficult to obtain high-quality images. For example, matching between slices constituting a CT image may not be easy. In order to solve such a problem, the guide rail 50 can be selectively installed. That is, the guide rail 50 can prevent the gantry 10 from moving when the gantry 10 is in direct contact with the floor, thereby minimizing an influence of a floor condition on the movement of the gantry 10.

The guide rail 50 can be stored in the inside of the gantry 10. Further, the guide rail 50 can be stored in a guide rail storage box (not shown) provided in the gantry 10. In certain embodiments, the guide rail 50 is stored separately from the gantry 10.

In certain embodiments, the guide rail 50 is formed as one unit having a predetermined length. Further, the guide rail 50 can be disassembled into a plurality of rail units (not shown) for easy storage. Further, the guide rail 50 can be formed, namely designed or constructed, to be foldable. Details about the guide rail 500 will be understood by referring to FIGS. 12 and 13.

The guide rail 50 includes a body 51 disposed on the floor, a head 52 configured to interact with a moving member 80, and a neck 53 connecting the body 51 to the head 52.

The medical device 1 further includes a belt 60 configured to guide a movement of the gantry 10 together with the guide rail 50.

In certain embodiments, the belt 60 is retractably installed in the gantry 10 so as to be pulled out.

The belt 60 can be pulled out of the gantry 10 to be parallel to the guide rail 50. In other words, the belt 60 can be installed in the gantry 10 to be pulled out in the extending direction L (see FIG. 5) of the guide rail 50.

In certain embodiments, the belt 60 includes a toothed belt.

The belt 60 can be positioned between the guide rail 50 and the caster 90 so as to be adjacent to the guide rail 50. More specifically, the belt 60 can be positioned between the guide rail 50 and the caster 90 so as to be adjacent to the neck 53 of the guide rail 50. In other words, the belt 60 and the guide rail 50 can be disposed adjacent to each other to appear as if they are in a single line. The alignment of the belt 60 and guide rail 50 is designed to prevent a safety accident, such as a user falling over the belt 60 when moving the gantry 10 along the guide rail 50.

The medical device 1 further includes a belt holder 70 (see FIG. 5) coupled to one end of the belt 60 to facilitate withdrawal of the belt 60. The belt holder 70 can be detachably installed in the gantry 10. The belt holder 70 will be described later in detail.

The medical device 1 further includes the moving member 80 installed in the gantry 10 to implement a movement of the gantry 10. The moving member 80 is able to move along the guide rail 50.

In certain embodiments, the moving member 80 is installed on the bottom face 13 of the gantry 10 so as to be movable along the guide rail 50. More specifically, the moving member 80 can be installed in a moving member mounting portion 13a that is recessed in the bottom face 13 of the gantry 10.

The moving member 80 is able to move along the guide rail 50 while remaining in contact with the guide rail 50.

The moving member 80 includes a housing 81. The housing 81 of the moving member 80 can be coupled to the gantry 10. More specifically, the housing 81 of the moving member 80 can be fixedly coupled with the moving member mounting portion 13a that is recessed in the bottom face 13 of the gantry 10.

The moving member 80 includes at least one chain 82 rotatably disposed inside the housing 81. In certain embodiments, the moving member 80 includes a pair of chains 82 that are rotatably disposed inside the housing 81. The at least one chain 82 can include a plurality of rollers 82a. More specifically, the at least one chain 82 can be formed by connecting the plurality of rollers 82a in the shape of a closed loop.

The moving member 80 further includes a rotation guide 83 configured to guide a rotation of the at least one chain 82. The at least one chain 82 is able to rotate along the outer circumferential surface of the rotation guide 83. The rotation guide 83 can include a shape extended so as to have a predetermined length in the extending direction L (see FIG. 5) of the guide rail 50. Further, the rotation guide 83 can include a circular cross-section. In certain embodiments, the rotation guide 83 is fixedly coupled in the inside of the housing 81 in such a way to be surrounded by the at least one chain 82.

The moving member 80 further includes a fixing member 84 for fixing the rotation guide 83 at the housing 81. In certain embodiments, the fixing member 84 includes a screw.

At least one chain 82 can move along the guide rail 50 in contact with the guide rail 50. More specifically, the at least one chain 82 is able to move along the guide rail 50 in contact with a portion of the head 52 of the guide rail 50. In this way, excessive friction between the at least one chain 82 and the guide rail 50 can be reduced by minimizing a contact area between the at least one chain 82 and the guide rail 50.

The medical device 1 further includes the caster 90 installed in the gantry 10 to allow the gantry 10 to move.

The caster 90 can be installed on the bottom face 13 of the gantry 10 so as to selectively contact the floor.

In certain embodiments, the caster 90 is rotatably installed on the bottom face 13 of the gantry 10. That is, the caster 90 can be installed on the bottom face 13 of the gantry 10 in such a way to be capable of changing directions.

In certain embodiments, the caster 90 is installed in the gantry 10 to protrude from the gantry 10. That is, the caster 90 can be installed on the bottom face 13 of the gantry 10 to protrude from the gantry 10.

The moving member 80 and the caster 90 can selectively provide mobility to the gantry 10. More specifically, when the moving member 80 is involved in the movement of the gantry 10, the caster 90 may not be involved in the movement of the gantry 10. Alternatively, when the caster 90 is involved in the movement of the gantry 10, the moving member 80 may not be involved in the movement of the gantry 10. That is, the moving member 80 can be involved in the movement of the gantry 10 when the object 20 is photographed, and the caster can be involved in the movement of the gantry 10 when the object 20 is not photographed.

When the object 20 is not photographed, the caster 90 may protrude from the gantry 10 to be involved in the movement of the gantry 10. When the object 20 is photographed, the caster 90 can be inserted into the inside of the gantry 10 so as not to be involved in the movement of the gantry 10.

The medical device 1 further includes a moving member driving unit 100 disposed in the inside of the gantry 10 to supply power to the moving member 80.

The medical device 1 further includes a movement preventing unit 200 disposed in the inside of the gantry 10 to prevent the moving member 80 from moving.

The moving member driving unit 100 and the movement preventing unit 200 are described in further detail herein below with respect to FIGS. 5, 8 and 10.

Figure 4:
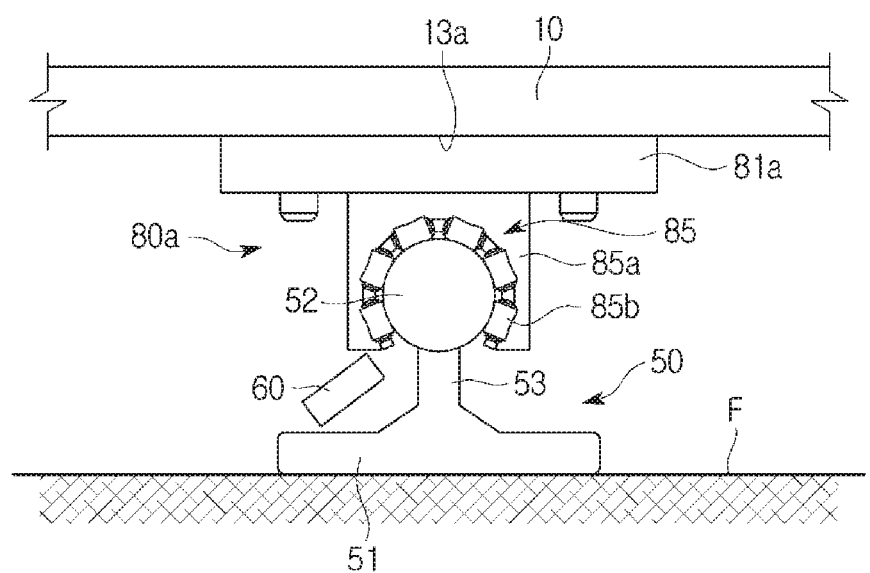
FIG. 4 is a view illustrating a mobility implementation structure of a gantry according to a second embodiment.

FIG. 4 is a view illustrating a mobility implementation structure of a gantry according to a second embodiment. Hereinafter, a description about the same configuration as that described above with reference to FIGS. 1 to 3 will be omitted. In FIG. 4, "F" refers to the floor.

In the example shown in FIG. 4, a moving member 80a includes a housing 81a. The housing 81a of the moving member 80a is coupled with the gantry 10. More specifically, the housing 81a of the moving member 80a can be fixedly coupled with the moving member mounting portion 13a recessed in the bottom face 13 of the gantry 10.

The moving member 80a further includes a slider 85 coupled to the inside of the housing 81a. The slider 85 includes a slider body 85a, and a plurality of rollers 85b coupled with the slider body 85a to be able to contact the guide rail 50. In another embodiment, the slider 85 includes the slider body 85a, and a plurality of balls coupled with the slider body 85a to be able to contact the guide rail 50.

The slider body 85a can be fixedly coupled to the inside of the housing 81a.

The slider 85 can be movably coupled with the guide rail 50. That is, the slider 85 is able to move along the guide rail 50 while being coupled with the guide rail 50. More specifically, the slider 85 can move along the guide rail 50 while being coupled with the head 52 of the guide rail 50.

Figure 5:
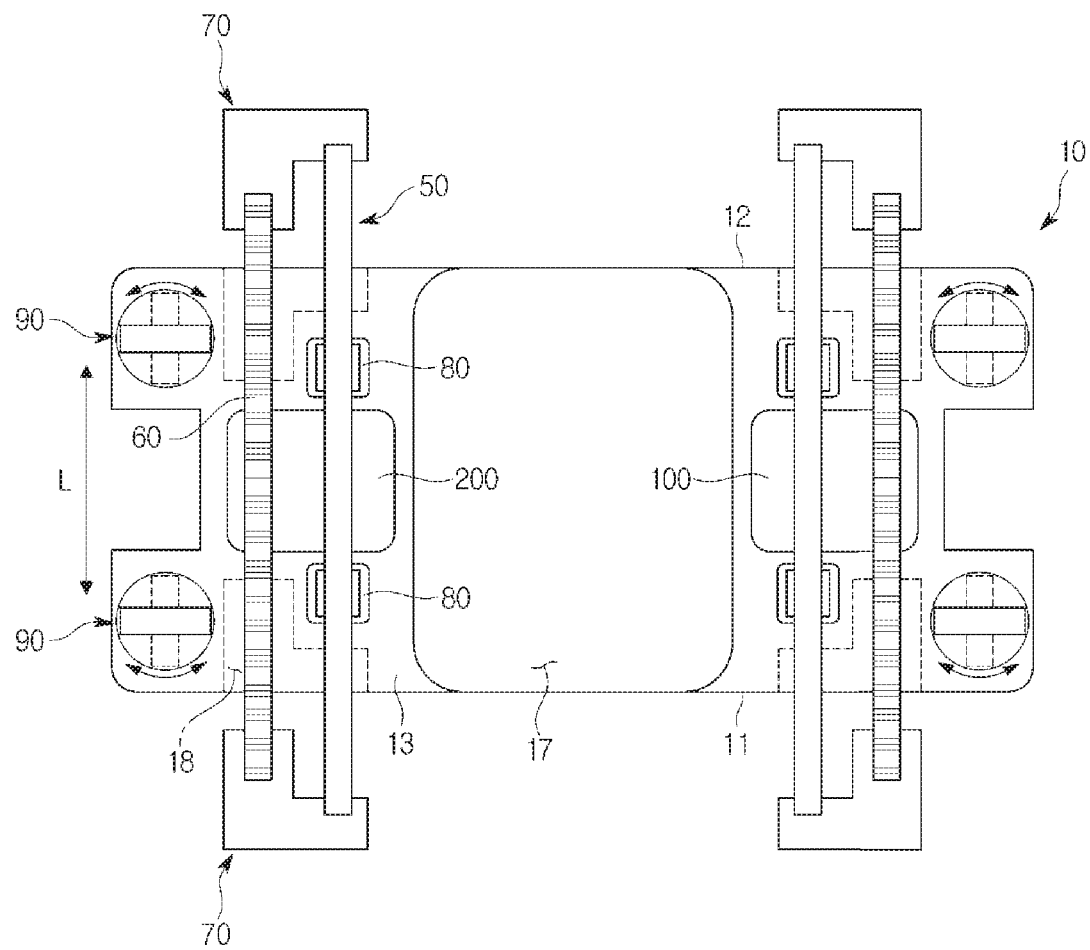
FIG. 5 is a bottom view illustrating a gantry disposed on a guide rail in a medical device, according to an embodiment of the present disclosure.

FIG. 5 is a bottom view illustrating a gantry disposed on a guide rail in a medical device, according to an embodiment of the present disclosure. FIG. 5 shows a case in which the mobility implementation structure of the gantry according to the first embodiment and the belt holder according to the first embodiment are applied. Hereinafter, reference numerals not denoted in FIG. 5 will be able to be understood from the above description with reference to FIGS. 1 to 3.

In the example shown in FIG. 5, a table inserting portion 17 is formed at the lower portion of the gantry 10 to allow a part of the table 30 to be inserted therein. As shown in FIG. 1, the table inserting portion 17 can be recessed in the bottom face 13 of the gantry 10.

The gantry 10 further includes a belt holder mounting portion 18. The belt holder mounting portion 18 can be recessed in the front face 11 and the rear face 12 of the gantry 10.

The belt holder 70 can be coupled to both ends of the belt 60 so that the belt 60 is easily drawn out. More specifically, the belt holder 70 can be coupled to one end of the belt 60 facing the front of the gantry 10 and the other end of the belt 60 facing the back of the gantry 10. Therefore, the belt 60 and the belt holder 70 can move integrally.

A moving member 80 can be installed inside the gantry 10. In certain embodiments, the medical device 1 includes a plurality of moving members 80. In certain embodiments, the medical device 1 includes a pair of first moving members disposed on the front side of the gantry 10, and a pair of second moving members disposed on the back side of the gantry 10. The pair of first moving members can be disposed on the right and left sides of the gantry 10, respectively, with the table inserting portion 17 as the center. The pair of second moving members can also be disposed on the right and the left sides of the gantry 10, respectively, with the table inserting portion 17 as the center.

The moving member driving unit 100 can be positioned between the first moving member and the second moving member, which are disposed on the right side of the gantry 10. The moving member driving unit 100 can be provided inside the gantry 10 so as to be positioned between the first moving member and the second moving member, which are disposed on the right side of the gantry 10.

The movement preventing unit 200 can be positioned between the first moving member and the second moving member, which are disposed on the left side of the gantry 10. The movement preventing unit 200 can be provided inside the gantry 10 so as to be positioned between the first moving member and the second moving member, which are disposed on the left side of the gantry 10.

The caster 90 can be installed on the outside of the gantry 10. In certain embodiments, the medical device 1 includes a plurality of casters 90. In certain embodiments, the medical device 1 includes a pair of first casters disposed on the front side of the gantry 10, and a pair of second casters disposed on the back side of the gantry 10. The pair of first casters can be disposed on the right and the left sides of the gantry 10, respectively, with the table inserting portion 17 as the center. The pair of second casters can also be disposed on the right and left sides of the gantry 10, respectively, with the table inserting portion 17 as the center.

The guide rail 50 can be installed at a position corresponding to the moving member 80. Therefore, the guide rail 50 can be positioned further inward of the gantry 10 than the belt 60.

The guide rail 50 can be detachably coupled to the belt holder 70. That is, the belt holder 70 can include a guide rail mounting portion 71a (see FIG. 6A). The guide rail 50 can be detachably coupled to the guide rail mounting portion 71a.

The belt 60 can be positioned between the moving member 80 and the caster 90.

In other words, the belt 60 can be positioned between the guide rail 50 and the caster 90 to be adjacent to the guide rail 50.

Figure 6A:
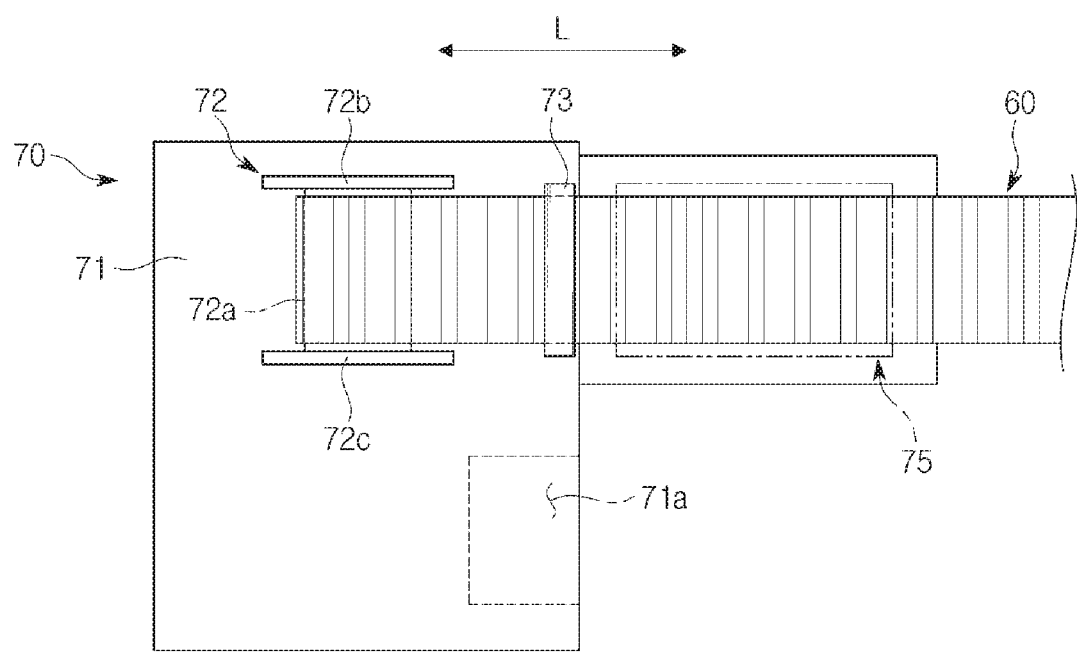
FIG. 6A is a top view illustrating a belt holder of the first embodiment in a medical device according to an embodiment of the present disclosure.
Figure 6B:
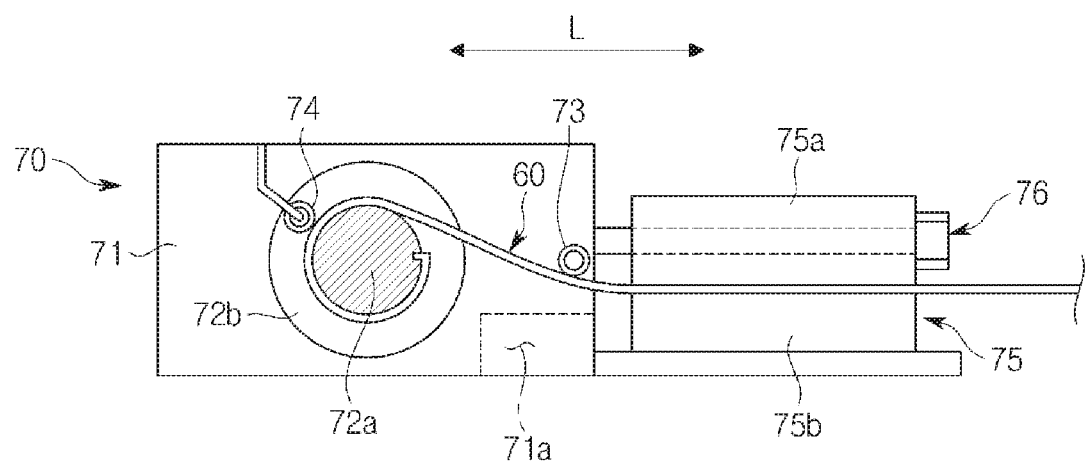
FIG. 6B is a side view illustrating a belt holder of the first embodiment in a medical device according to an embodiment of the present disclosure.

FIG. 6A is a top view illustrating a belt holder of the first embodiment in a medical device according to an embodiment of the present disclosure, and FIG. 6B is a side view illustrating a belt holder of the first embodiment in a medical device according to an embodiment of the present disclosure. Hereinafter, reference numerals not denoted in FIGS. 6A and 6B will be able to be understood from the above description with reference to FIGS. 1 to 3 and 5. For convenience of explanation, FIG. 6A is illustrated in a state in which a second guide roller 74 is omitted, and FIG. 6B is illustrated in a state in which a second supporting portion 72c is omitted.

In the examples shown in FIGS. 6A and 6B, the belt holder 70 includes a belt holder body 71 forming the outer appearance of the belt holder 70.

The belt holder 70 further includes a belt winder 72 installed inside the belt holder body 71. The belt winder 72 can be rotatably installed inside the belt holder body 71 so that the belt 60 is wound. In certain embodiments, the belt winder 72 includes a winding portion 72a that is in the shape of a cylinder and around which the belt 60 is wound, and a plurality of supporting portions 72b and 72c configured to support the winding portion 72a. The plurality of supporting portions 72b and 72c include a first supporting portion 72b for supporting one side of the winding portion 72a, and the second supporting portion 72c for supporting the other side of the winding portion 72a. One end of the belt 60 can be fixed at the winding portion 72a.

The belt holder 70 further includes a plurality of guide rollers 73 and 74 installed inside the belt holder body 71 to guide a movement of the belt 60 wound around the belt winder 72. The plurality of guide rollers 73 and 74 includes a first guide roller 73 for primarily guiding the belt 60 being drawn into the belt holder body 71, and a second guide roller 74 for secondly guiding the belt 60 being drawn into the belt holder body 71. The second guide roller 74 can be adjacent to the winding portion 72a of the belt winder 72.

The belt holder 70 further includes a belt clamp 75 installed on one side of the belt holder body 71 facing the gantry 10 to guide the movement of the belt 60. The belt clamp 75 can be installed on one side of the belt holder body 71 facing the gantry 10 to guide the movement of the belt 60 drawn into the belt holder body 71. The belt clamp 75 includes a first plate 75a for guiding the movement of the belt 60 at the upper portion of the belt 60, and a second plate 75b for guiding the movement of the belt 60 at the lower portion of the belt 60. That is, the belt 60 can be movable between the first plate 75a and the second plate 75b. At this time, the belt 60 can be guided by the belt clamp 75 with a predetermined tension.

The belt holder 70 further includes a tension adjusting member 76 configured to adjust the tension of the belt 60 guided by the belt clamp 75. The tension adjusting member 76 can be coupled to the belt clamp 75 to adjust the tension of the belt 60. More specifically, the tension adjusting member 76 can be coupled to the first plate 75a of the belt claim 75 to adjust the tension of the belt 60. The tension adjusting member 76 can be in the shape of a bolt. However, the shape of the tension adjusting member 76 is not limited to the above example, and can be variously modified.

Figure 7A:
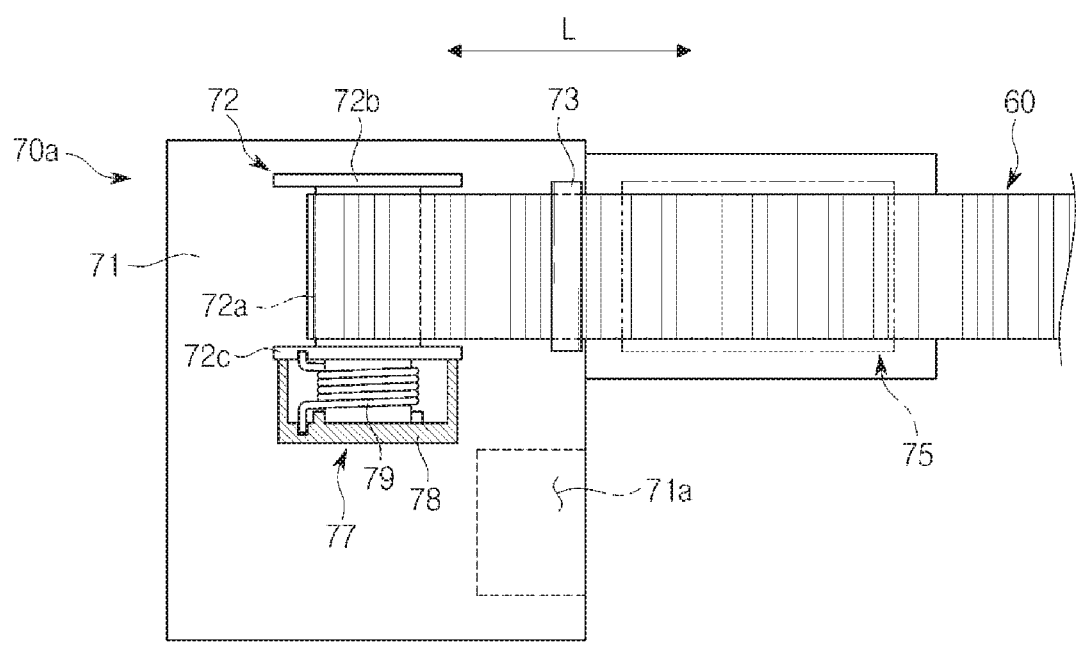
FIG. 7A is a top view illustrating a belt holder of the second embodiment in a medical device according to an embodiment of the present disclosure.
Figure 7B:
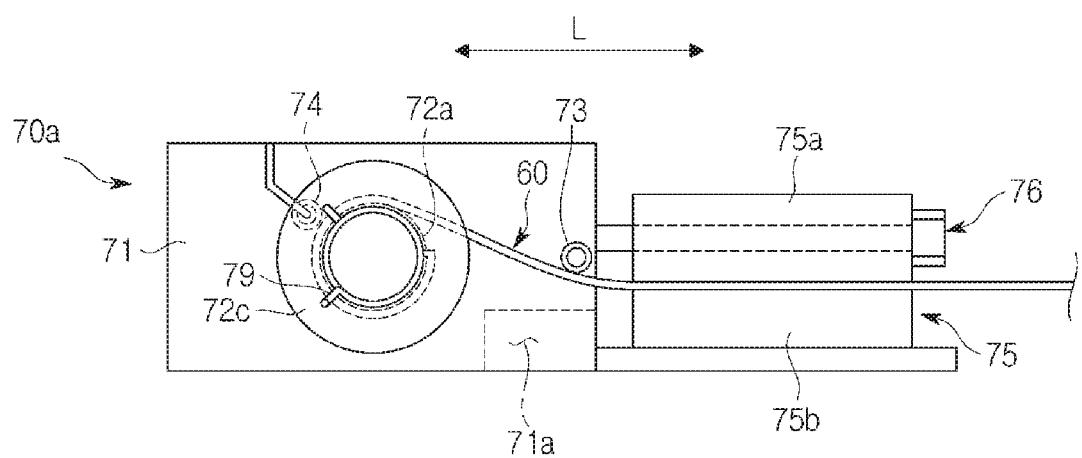
FIG. 7B is a side view illustrating a belt holder of the second embodiment in a medical device according to an embodiment of the present disclosure.

FIG. 7A is a top view illustrating a belt holder of the second embodiment in a medical device according to an embodiment of the present disclosure, and FIG. 7B is a side view illustrating a belt holder of the second embodiment in a medical device according to an embodiment of the present disclosure. Hereinafter, reference numerals not denoted in FIGS. 7A and 7B will be able to be understood from the above description with reference to FIGS. 1 to 3 and 5. Hereinafter, a description about the same configuration as that described above with reference to FIGS. 6A and 6B will be omitted. For convenience of explanation, FIG. 7A is illustrated in a state in which a second guide roller 74 is omitted, and FIG. 7B is illustrated in a state in which the first supporting portion 72b and the casing 78 of the belt winder driving unit 77 are omitted.

In the examples shown in FIGS. 7A and 7B, a belt holder 70a includes a belt holder body 71 forming the outer appearance of the belt holder 70a.

The belt holder 70a further includes a belt winder 72 installed inside the belt holder body 71. The belt winder 72 can be rotatably installed inside the belt holder body 71 so that the belt 60 is wound. The belt winder 72 includes a winding portion 72a that is in the shape of a cylinder and around which the belt 60 is wound, and a plurality of supporting portions 72b and 72c configured to support the winding portion 72a. The plurality of supporting portions 72b and 72c includes the first supporting portion 72b for supporting one side of the winding portion 72a, and a second supporting portion 72c for supporting the other side of the winding portion 72a. One end of the belt 60 can be fixed at the winding portion 72a.

The belt holder 70a further includes a plurality of guide rollers 73 and 74 installed inside the belt holder body 71 to guide a movement of the belt 60 wound around the belt winder 72. The plurality of guide rollers 73 and 74 includes a first guide roller 73 for primarily guiding the belt 60 being drawn into the belt holder body 71, and a second guide roller 74 for secondly guiding the belt 60 being drawn into the belt holder body 71. The second guide roller 74 can be disposed adjacent to the winding portion 72a of the belt winder 72.

The belt holder 70a further includes a belt winder driving unit 77 installed inside the belt holder body 71 to rotate the belt winder 72 by using an elastic force.

The belt winder driving unit 77 includes a casing 78 having an open side facing the belt winder 72. More specifically, the belt winder driving unit 77 includes the casing 78 having an open side facing the second supporting portion 72c of the belt winder 72.

The belt winder driving unit 77 further includes an elastic member 79 that can be elastically deformed. The elastic member 79 can be accommodated inside the casing 78. One end of the elastic member 79 can be fixedly coupled to the casing 78, and the other end of the elastic member 79 can be fixedly coupled to the belt winder 72. More specifically, the other end of the elastic member 79 can be fixedly coupled to the second supporting portion 72c of the belt winder 72. Therefore, the other end of the elastic member 79 can rotate integrally with the belt winder 72.

In certain embodiments, the elastic member 79 includes a torsion spring.

When the belt holder 70a is pulled out of the gantry 10, the belt 60 wound around the belt winder 72 can be unwound to extend in the extending direction L of the guide rail 50. At this time, a tension is applied to the elastic member 79. The belt 60 pulled out of the belt holder body 71 can be re-wound around the belt winder 72 by the resilience of the elastic member 79. The belt 60 pulled out of the gantry 10 can be re-wound around the belt winder 72 by the resilience of the elastic member 79.

The belt holder 70a further includes a belt clamp 75 installed on one side of the belt holder body 71 facing the gantry 10 to guide a movement of the belt 60. A further description about the belt clamp 75 will be omitted because it has been described above with reference to FIGS. 6A and 6B.

Figure 8:
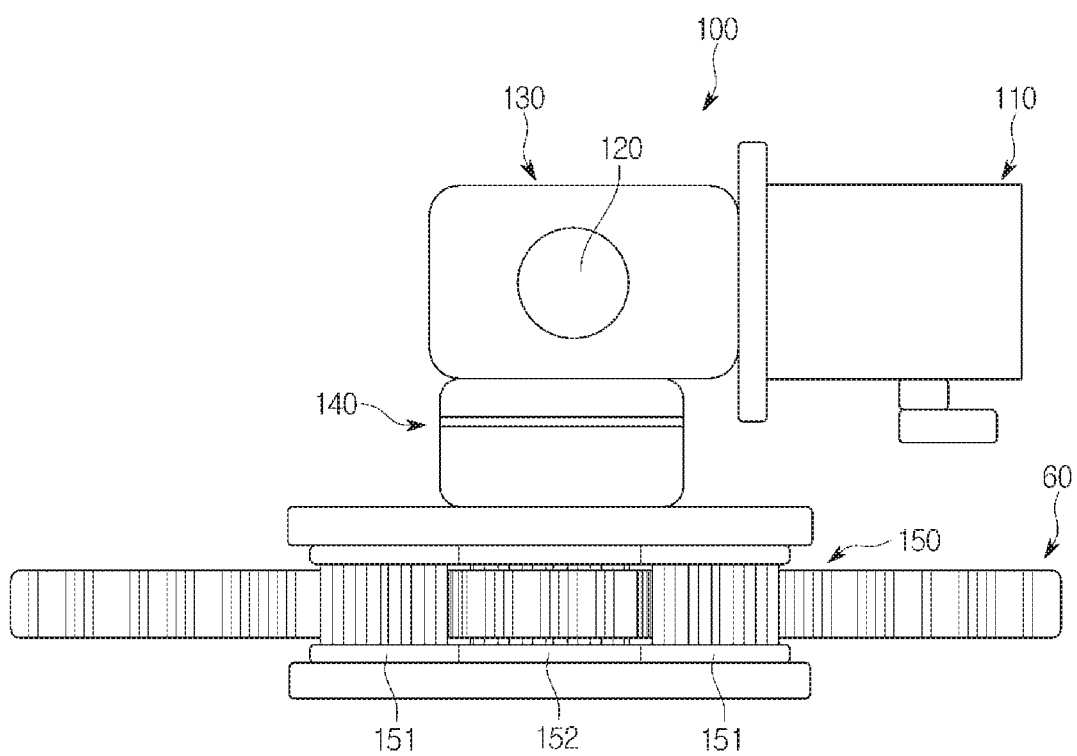
FIG. 8 is a top view illustrating a moving member driving unit in a medical device according to an embodiment of the present disclosure.
Figure 9:
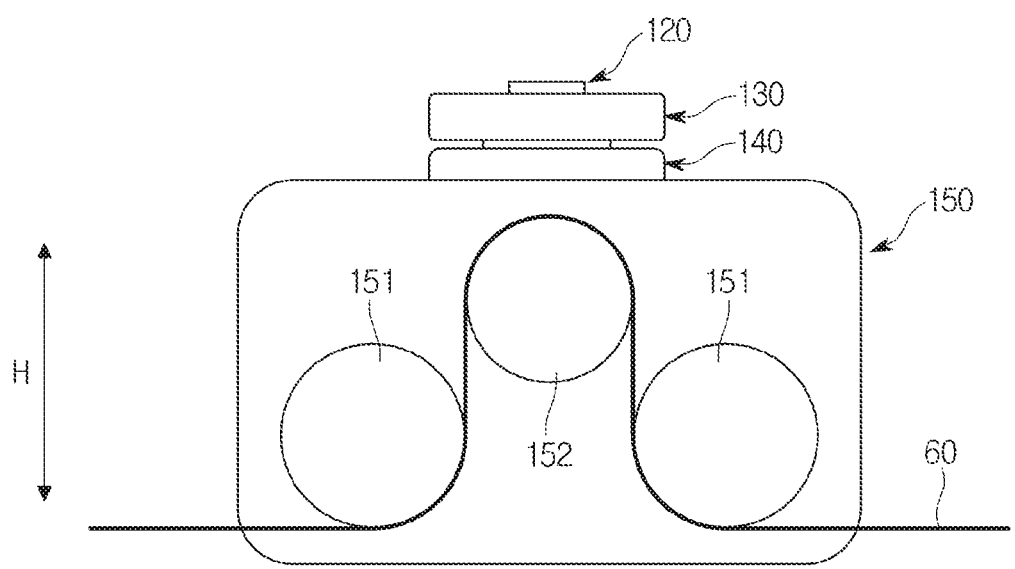
FIG. 9 is a front view illustrating a moving member driving unit in a medical device according to an embodiment of the present disclosure.

FIG. 8 is a top view illustrating a moving member driving unit in a medical device according to an embodiment of the present disclosure, and FIG. 9 is a front view illustrating a moving member driving unit in a medical device according to an embodiment of the present disclosure. Hereinafter, reference numerals not denoted in FIGS. 8 and 9 will be able to be understood from the above description with reference to FIGS. 1 to 3 and 5. Hereinafter, the medical device to which the mobility implementation structure of the gantry according to the first embodiment and the belt holder according to the first embodiment are applied will be described.

In the examples shown in FIGS. 8 and 9, the medical device 1 includes the moving member driving unit 100 provided inside the gantry 10 to supply power to the moving member 80.

In certain embodiments, the moving member driving unit 100 includes a motor 110 for generating a rotational force for a rotating shaft 120.

The moving member driving unit 100 further includes the rotating shaft 120 connecting the motor 110 to the moving member 80.

The moving member driving unit 100 further includes a gear box 130 having various gears therein. The various gears function to transfer power required to rotate the rotating shaft 120.

The moving member driving unit 100 further includes a clutch 140 configured to cause power of the motor 110 to be transferred to the moving member 80 or to prevent the power of the motor 110 from being transferred to the moving member 80.

The moving member driving unit 100 further includes an encoder, a brake, and the like.

The medical device 1 further includes a first pulley unit 150 installed adjacent to the moving member driving unit 100 to guide a movement of the belt 60 inside the gantry 10. In certain embodiments, the first pulley unit 150 includes a plurality of idler pulleys 151, and a drive pulley 152 positioned above the plurality of idler pulleys 151 in a height direction H (see FIG. 1) of the gantry 10. In certain embodiments, the first pulley unit 150 includes two idler pulleys 151 and one drive pulley 152.

Figure 10:
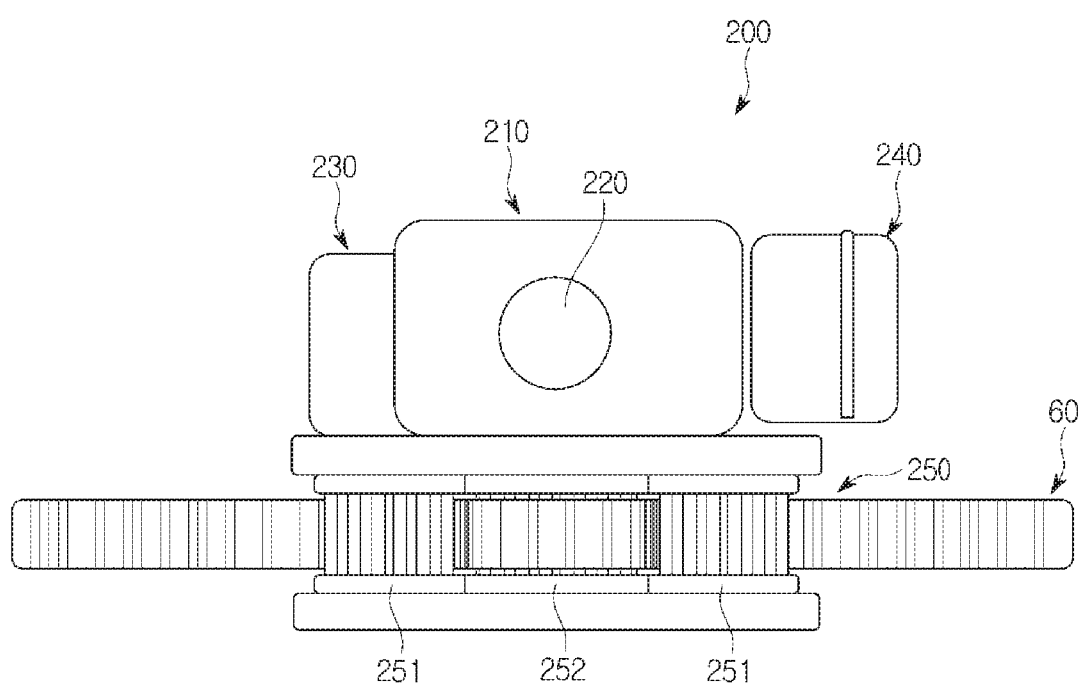
FIG. 10 is a top view illustrating a movement preventing unit in a medical device according to an embodiment of the present disclosure.

FIG. 10 is a top view illustrating a movement preventing unit in a medical device according to an embodiment of the present disclosure. Hereinafter, reference numerals not denoted in FIG. 10 will be able to be understood from the above description with reference to FIGS. 1 to 3 and 5. Hereinafter, the medical device to which the mobility implementation structure of the gantry according to the first embodiment and the belt holder according to the first embodiment are applied will be described. Hereinafter, a front view of the movement preventing unit 200 is the same as that shown in FIG. 9, and accordingly, the front view of the movement preventing unit 200 will be omitted.

In the example shown in FIG. 10, the medical device 1 further includes the movement preventing unit 200 provided inside the gantry 10 to prevent the moving member 80 form moving. The movement preventing unit 200 can operate when it is necessary to prevent the moving member 80 from moving for safety reasons.

In certain embodiments, the movement preventing unit 200 includes a gear box 210 having various gears therein. The various gears function to transfer power required to rotate a rotating shaft 220.

The movement preventing unit 200 further includes an encoder 230, a brake 240, and the like.

The medical device 1 further includes a second pulley unit 250 installed adjacent to the movement preventing unit 200 to guide a movement of the belt 60 inside the gantry 10. In certain embodiments, the second pulley unit 250 includes a plurality of idler pulleys 251, and a drive pulley 252 positioned above the plurality of idler pulleys 251 in the height direction H (see FIG. 1) of the gantry 10. In certain embodiments, the second pulley unit 250 includes two idler pulleys 251 and one drive pulley 252.

Figure 11B:
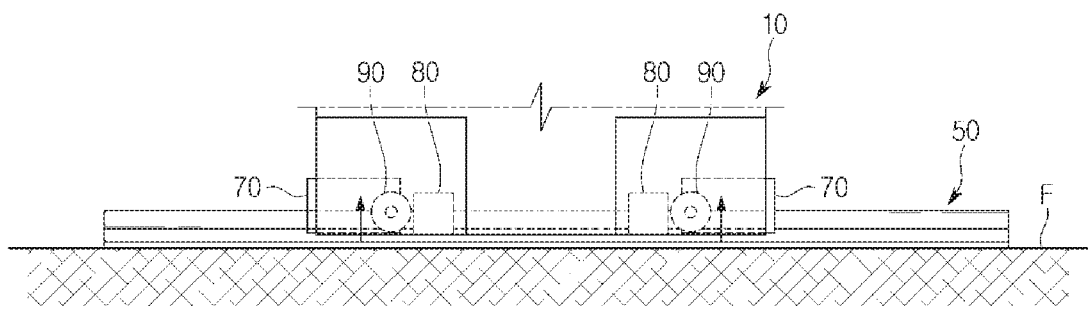
Figure 11C:
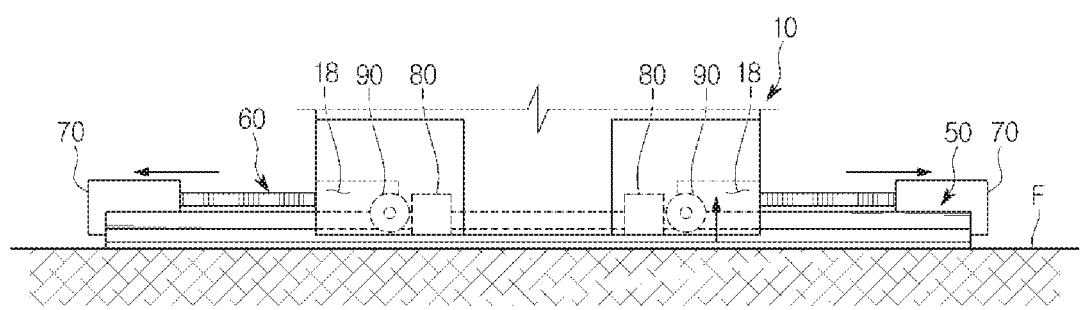

FIG. 11A to 11C are views illustrating a movement process of a gantry in a medical device according to an embodiment of the present disclosure. Hereinafter, reference numerals not denoted in FIGS. 11A to 11C will be able to be understood from the above description with reference to FIGS. 1 to 3 and 5. A reference numeral "F" refers to the floor. Hereinafter, the medical device to which the mobility implementation structure of the gantry according to the first embodiment and the belt holder according to the first embodiment are applied will be described.

When the object 20 is not photographed, the movement of the gantry 10 can be implemented by the caster 90. When the object 20 is not photographed, the moving member 80 may not participate in the movement of the gantry 10, and the guide rail 50 may be also unnecessary.

Hereinafter, the movement process of the gantry 10 when the object 20 is photographed will be described.

When the user wants to photograph the object 20 while moving the gantry 10, the guide rail 50 can be installed on the floor.

When the guide rail 50 is installed on the bottom surface, the movement of the gantry 10 can be implemented by an interaction of the moving member 80 and the guide rail 50. At this time, the caster 90 can be inserted inward of the gantry 10 to be spaced from the bottom surface. That is, the caster 90 may not participate in the movement of the gantry 10 when the object 20 is photographed.

The belt holder 70 can be pulled out of the gantry 10 so that the movement of the gantry 10 can be implemented more stably before the gantry 10 is moved, and the guide rail 50 can be coupled to the guide rail mounting portion 71*a* of the belt holder 70. Thereafter, the gantry 10 can be moved to photograph the object 20. At this time, since the gantry 10 can be stably guided by the guide rail 50 and the belt 60, it is possible to accurately and precisely photograph the object 20.

When photographing the object 20 is completed, the guide rail 50 can be removed from the floor.

Figure 12:
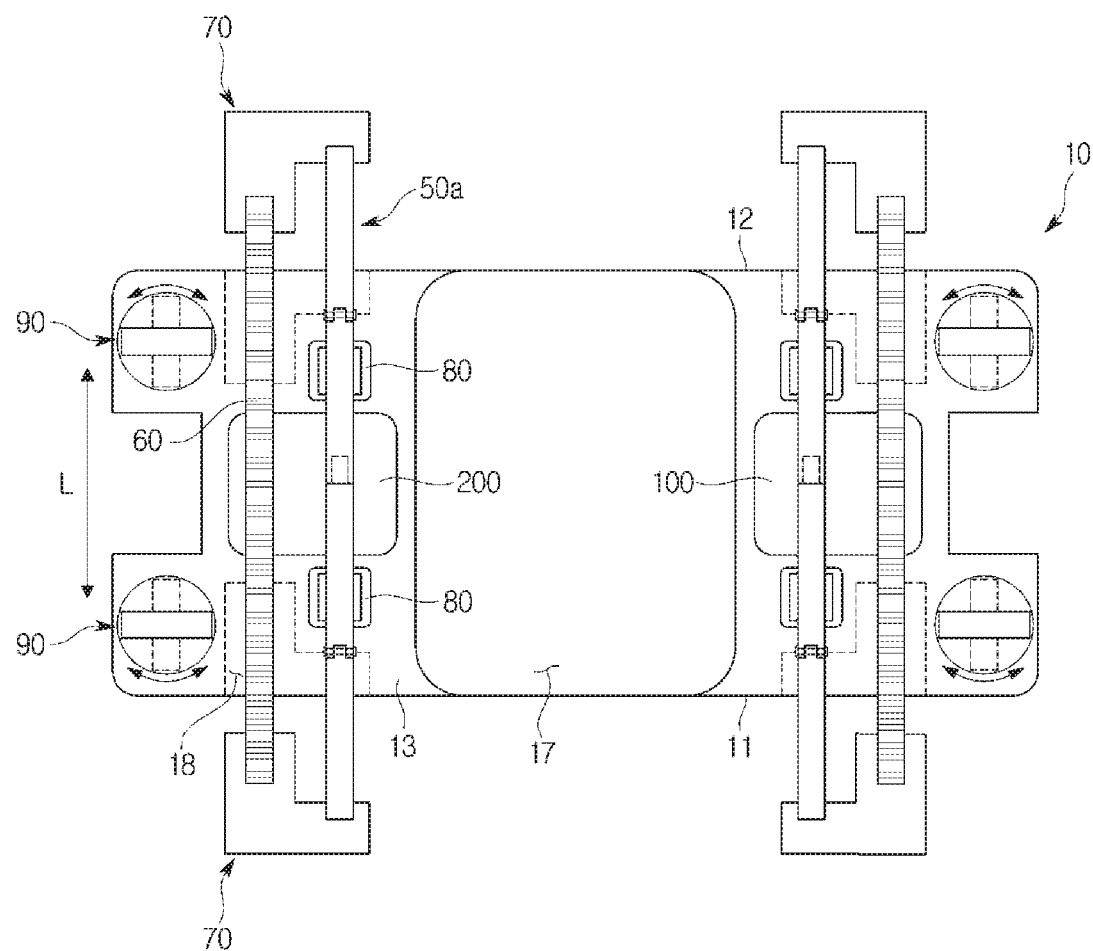
FIG. 12 is a bottom view illustrating a gantry disposed on a foldable guide rail in a medical device according to another embodiment of the present disclosure.
Figure 13:
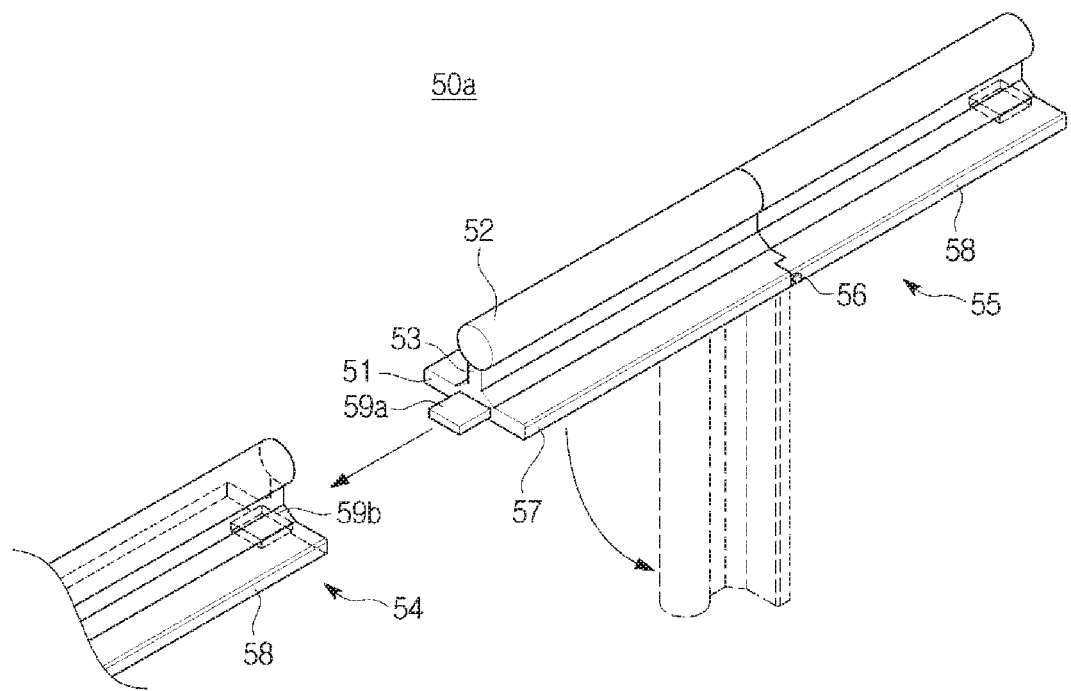
FIG. 13 is a view illustrating the foldable guide rail illustrated in FIG. 12.

FIG. 12 is a bottom view illustrating a gantry disposed on a foldable guide rail in a medical device according to another embodiment of the present disclosure, and FIG. 13 is a view illustrating the foldable guide rail illustrated in FIG. 12. A medical device 1*a* shown in FIG. 12 can have the same structure as the medical device 1 shown in FIGS. 1 to 11C except for the structure of a guide rail. Therefore, the structure of the guide rail will be mainly described below. Hereinafter, reference numerals not denoted in FIGS. 12 and 13 will be able to be understood from the above description with reference to FIGS. 1 to 11C.

In the examples shown in FIGS. 12 and 13, the medical device 1*a* further includes a guide rail 50*a* installed when the gantry 10 is moved to guide a movement of the gantry 10.

The guide rail 50*a* can be selectively installed on the floor as required. More specifically, the guide rail 50*a* can be selectively installed depending on the condition of the floor.

The guide rail 50*a* can be stored inside the gantry 10. Further, the guide rail 50*a* can be stored in a guide rail storage box (not shown) provided in the gantry 10. Further, the guide rail 50*a* can be stored separately from the gantry 10.

The guide rail 50*a* can be disassembled into a plurality of rail units 54 and 55 for easy storage. As an example, the guide rail 50*a* can include a first rail unit 54, and a second rail unit 55 coupled to the first rail unit 54 to form one guide rail 50*a*.

The guide rail 50*a* can be foldable. In other words, the guide rail 50*a* can be folded by rotating with respect to a rotating shaft 56.

More specifically, the guide rail 50*a* includes the plurality of rail units 54 and 55 which are coupled to each other to form one guide rail 50*a*. Each of the plurality of rail units 54 and 55 can be rotatable with respect to the rotating shaft 56, and can be foldable for easy storage. As an example, the plurality of rail units 54 and 55 can include the first rail unit 54 positioned in front of the medical device 1*a*, and the second rail unit 55 positioned behind the medical device 1*a* and detachably coupled to the first rail unit 54. Each of the first rail unit 54 and the second rail unit 55 can include a first rail 57 positioned in front of the medical device 1*a*, and a second rail 58 positioned behind the medical device 1*a* and rotatably coupled to the first rail 57 by the rotating shaft 56. A protrusion 59*a* can be provided on any one of the second rail 58 of the first rail unit 54 and the first rail 57 of the second rail unit 55. A coupling groove 59*b*, to which the protrusion 59*a* is coupled, can be provided on the other one of the second rail 58 of the first rail unit 54 and the first rail 57 of the second rail unit 55. The first rail unit 54 and the second rail unit 55 can be coupled to each other by a coupling of the protrusion 59*a* and the coupling groove 59*b*.

Through the structure, the guide rail 50*a* can be folded and disassembled.

The guide rail 50*a* further includes the body 51 disposed on the floor, the head 52 configured to interact with the moving member 80, and the neck 53 connecting the body 51 to the head 52.

Figure 14:
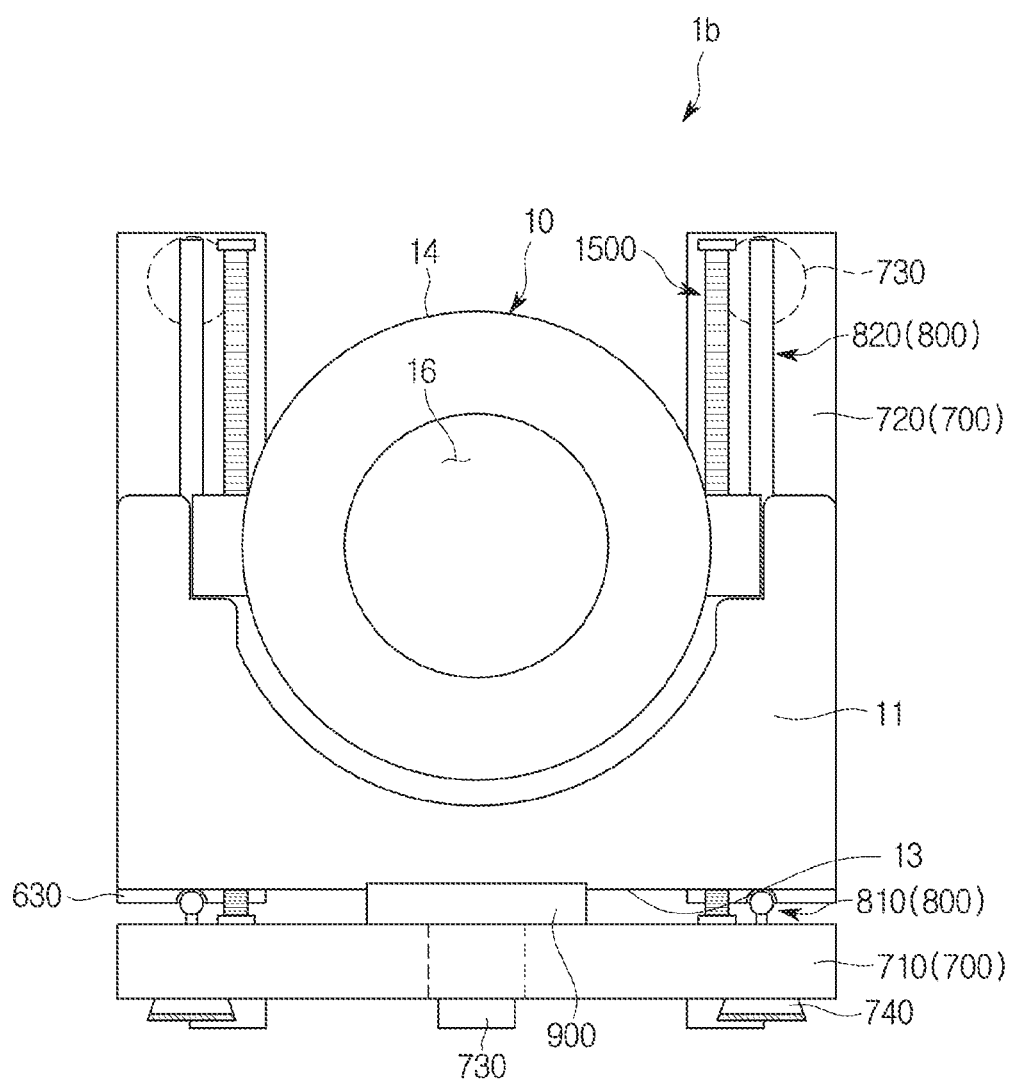
FIG. 14 is a view illustrating a medical device according to still another embodiment of the present disclosure.
Figure 15:
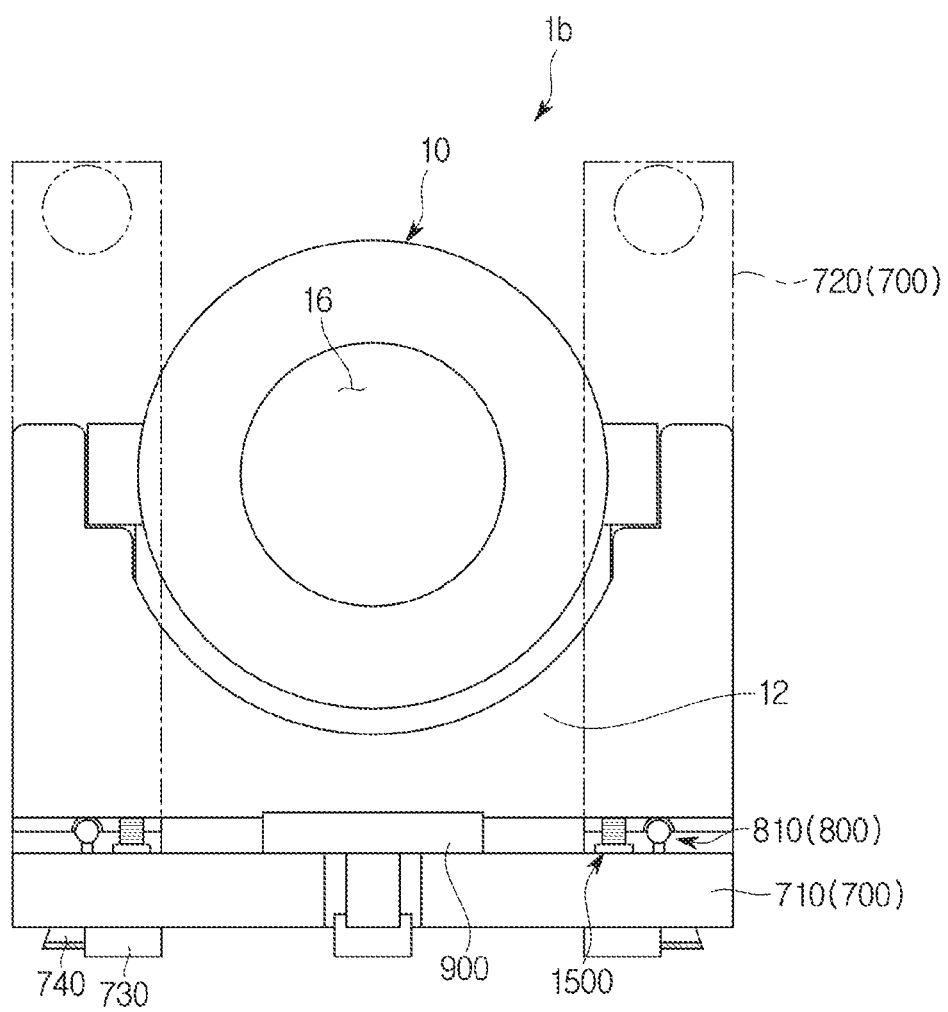
FIG. 15 is a view illustrating a state in which a platform leg is folded in a medical device according to still another embodiment of the present disclosure.
Figure 16:
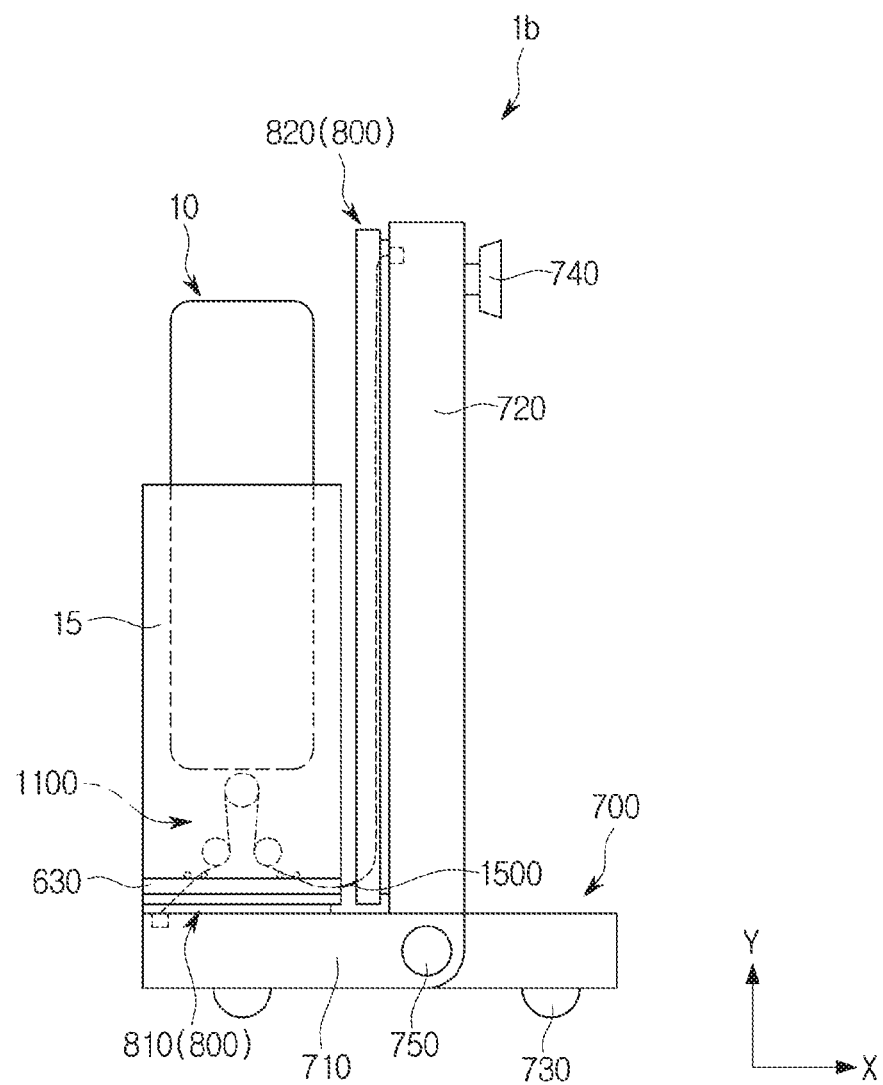
FIG. 16 is a view illustrating a state in which a platform leg is folded at an angle that is different from that of FIG. 15 in a medical device according to still another embodiment of the present disclosure.
Figure 17:
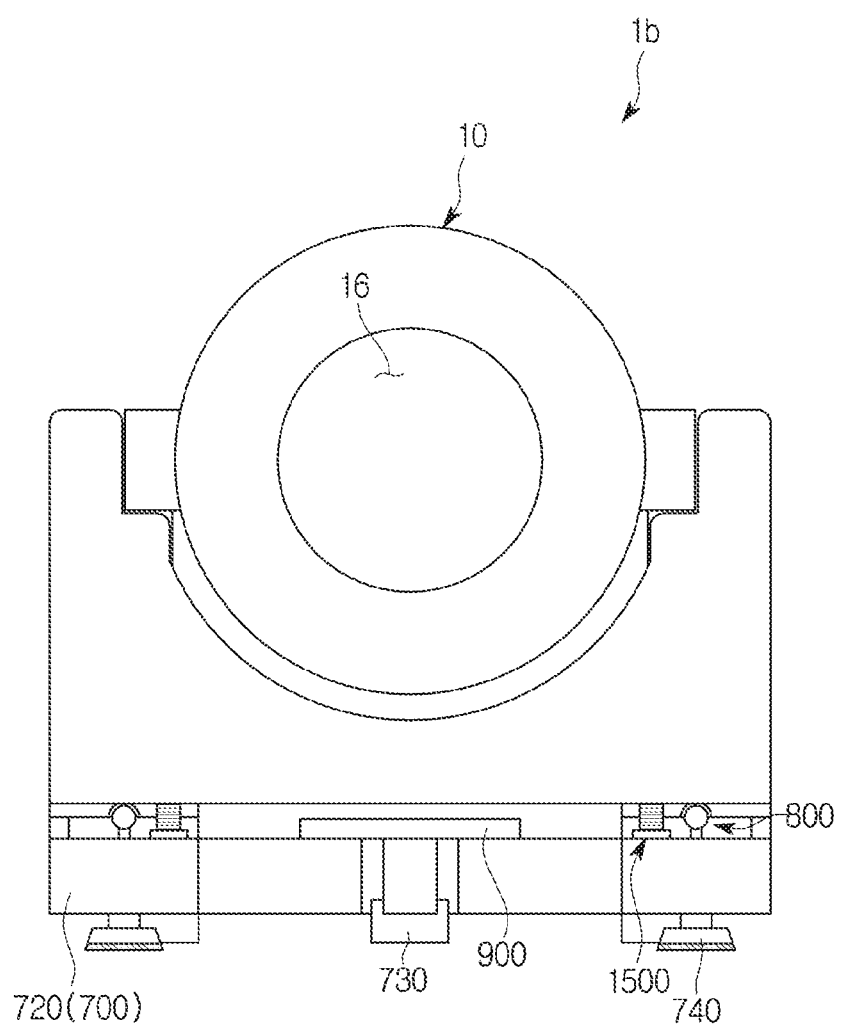
FIG. 17 is a view illustrating a state in which a platform leg is unfolded in a medical device according to still another embodiment of the present disclosure.
Figure 18A:
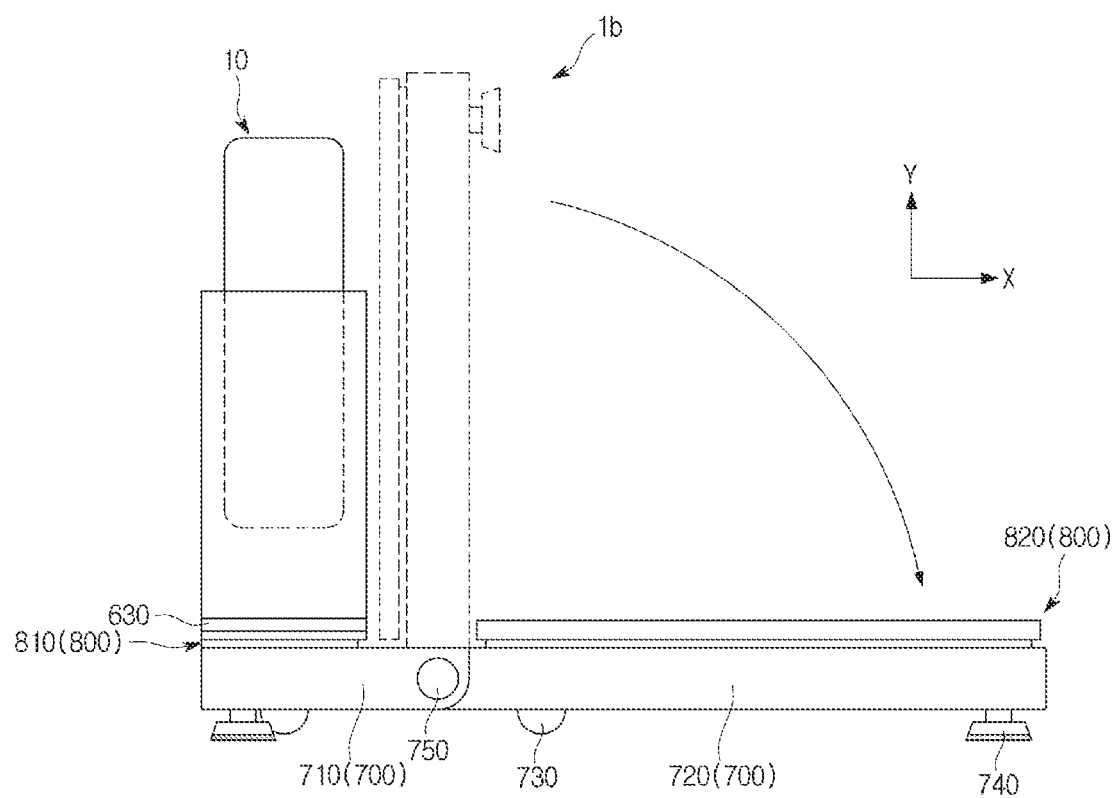
FIGS. 18A and 18B are views illustrating a process of coupling a first guide rail with a second guide rail after unfolding a platform leg in a medical device according to still another embodiment of the present disclosure.
Figure 18B:
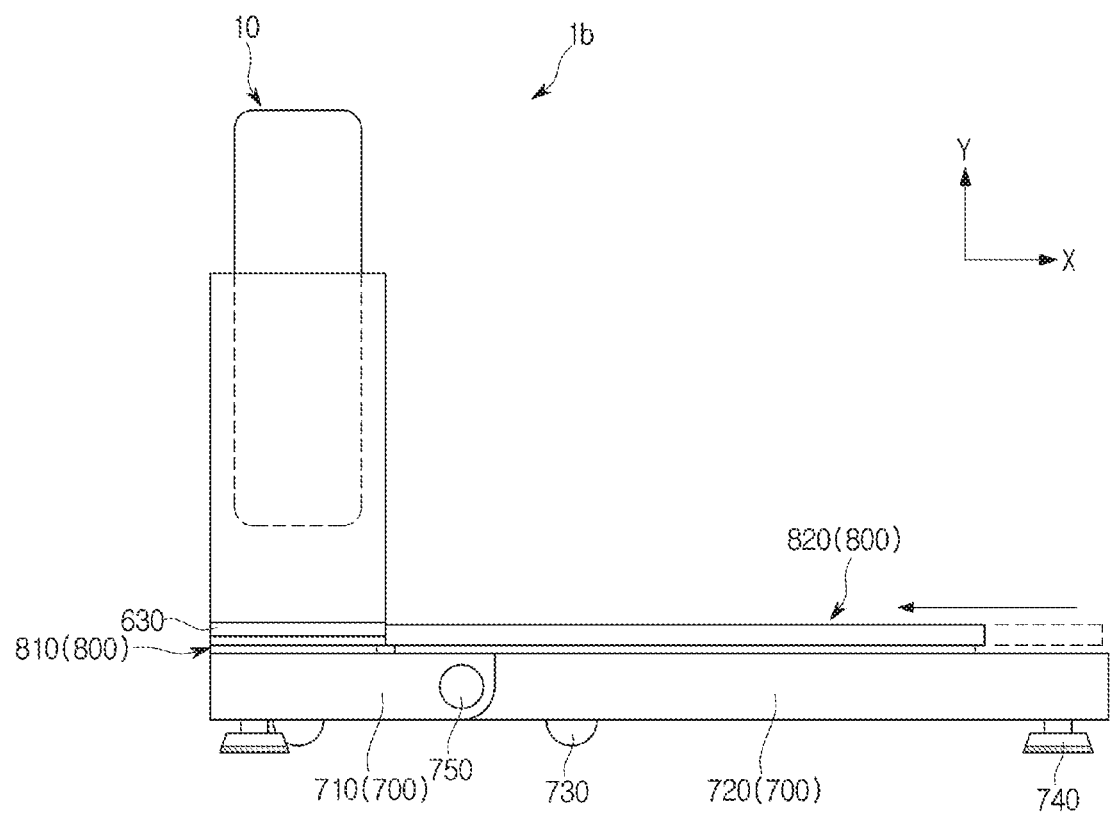

FIG. 14 is a view illustrating a medical device according to still another embodiment of the present disclosure, and FIG. 15 is a view illustrating a state in which a platform leg is folded in a medical device according to still another embodiment of the present disclosure. FIG. 16 is a view illustrating a state in which a platform leg is folded at an angle that is different from that of FIG. 15 in a medical device according to still another embodiment of the present disclosure, and FIG. 17 is a view illustrating a state in which a platform leg is unfolded in a medical device according to still another embodiment of the present disclosure. FIGS. 18A and 18B are views illustrating a process of coupling a first guide rail with a second guide rail after unfolding a platform leg in a medical device according to still another embodiment of the present disclosure. Hereinafter, reference numerals not denoted in FIGS. 14 to 18B will be able to be understood from the above description with reference to FIGS. 1 to 11C.

In the example shown in FIGS. 14 to 18B, a medical device 1*b* includes the gantry 10. The X-ray source to generate a X-ray and to radiate it to the object 20, and the X-ray detector to detect the X-ray transmitted through the object 20 and to acquire X-ray data can be provided inside the gantry 10.

In certain embodiments, the gantry 10 includes the front face 11 facing the object 20, the rear face 12 corresponding to the front face 11, the bottom face 13 facing the surface (hereinafter referred to as a floor) on which the gantry 10 moves, the top face 14 corresponding to the bottom face 13 and, the side face 15 connecting the front face 11, the rear face 12, the bottom face 13 and the top face 14.

The gantry 10 further includes the bore 16. The object 20 can be inserted into the bore 16. The object 20 can be photographed when the object 20 is inserted into the bore 16.

In certain embodiments, the gantry 10 is movable.

The gantry 10 can be installed on a moving platform 700 to be movable along a guide rail 800.

The medical device 1*b* further includes the moving platform 700 disposed below the gantry 10. In certain embodiments, the moving platform 700 includes a platform body 710 on which a plurality of casters 730 are installed. More specifically, the plurality of casters 730 can be installed on a bottom face of the platform body 710. The plurality of casters 730 can be installed in the platform body 710 to selectively protrude from the platform body 710. Further, the moving platform 700 further includes a platform leg 720 coupled to the platform body 710 to be foldable. In other words, the platform leg 720 can be rotatably coupled to the platform body 710.

The medical device 1b further includes the guide rail 800 installed on the moving platform 700 to guide a movement of the gantry 10. In other words, the guide rail 800 can be installed on the moving platform 700 to guide a movement of the gantry 10 moving on the moving platform 700. The guide rail 800 can extend on the platform body 710 and the platform leg 720. Preferably, the guide rail 800 can extend discontinuously on the platform body 710 and the platform leg 720. In certain embodiments the guide rail 800 includes a first guide rail 810 installed on the platform body 710. The guide rail 800 further includes a second guide rail 820 installed on the platform leg 720 so as to be detachably coupled to the first guide rail 810.

The medical device 1b further includes a belt 1500 installed to guide a movement of the gantry 10 together with the guide rail 800. That is, the belt 1500 can be installed to guide a movement of the gantry 10 together with the guide rail 800. The belt 1500 can be installed on the moving platform 700 so as to be adjacent to the guide rail 800. The belt 1500 and the guide rail 800 can be spaced apart from each other by a predetermined distance so as not to interfere with each other. The belt 1500 can be positioned inward of the guide rail 800. Both ends of the belt 1500 can be fixed at the moving platform 700. More specifically, one end of the belt 1500 can be fixed at the platform body 710. The other end of the belt 1500 can be fixed at the platform leg 720.

In certain embodiments, the belt 1500 includes a toothed belt.

The medical device 1b further includes a locking member 900 configured to selectively lock the gantry 10 to the moving platform 700. That is, the locking member 900 can be provided to selectively lock the gantry 10 to the moving platform 700. The locking member 900 can be disposed between the gantry 10 and the moving platform 700. In certain embodiments, the locking member 900 is installed on the moving platform 700 so as to be detachable from the gantry 10. However, the position of the locking member 900 is limited to the above example, and various embodiments can be used. As an example, the locking member 900 can be installed in the gantry 10 to be detachable from the moving platform 700. The locking member 900 can restrict the movement of the gantry 10 by coupling the gantry 10 to the moving platform 700. The gantry 10 can be movable when a locked state by the locking member 900 is released.

The medical device 1b further includes a plurality of supporting members 740.

The plurality of supporting members 740 can be installed on the lower surface of the moving platform 700. The plurality of supporting members 740 can serve to fix the moving platform 700. In certain embodiments, the plurality of supporting members 740 includes an anti-skid portion (not shown) to prevent the moving platform 700 from sliding on the floor. The anti-skid portion can be formed on the plurality of supporting members 740 so as to be in contact with the floor, and can have an elastic material. For example, the anti-skid portion can be formed of rubber, silicon, urethane, and the like.

The plurality of casters 730 can be involved in a movement of the moving platform 700. The plurality of supporting members 740 can be involved in fixing the moving platform 700. In other words, the plurality of casters 730 and the plurality of supporting members 740 can selectively contact the floor. When the moving platform 700 is moved, the plurality of casters 730 can be in contact with the floor. Alternatively, when the moving platform 700 is fixed, the plurality of supporting members 740 can be in contact with the floor.

The medical device 1b further includes a belt movement-involved module configured to be involved in moving the belt 1500. The belt movement-involved module can be installed inside the gantry 10.

In certain embodiments, the belt movement-involved module includes a pulley unit 1100.

In certain embodiments, the gantry 10 includes a slider 630. The slider 630 can be formed on one side of the gantry 10 facing the guide rail 800. The slider 630 can include a slider body (not shown), and a plurality of rollers (not shown) coupled to the slider body to be able to contact the guide rail 800. As another example, the slider 630 can include the slider body, and a plurality of balls (not shown) coupled to the slider body to be able to contact the guide rail 800.

The slider 630 can be movably coupled to the guide rail 800. In other words, the slider 630 can move along the guide rail 800 while being coupled to the guide rail 800.

The platform leg 720 of the moving platform 700 can be foldably installed. In other words, the platform leg 720 can be installed on the platform body 710 so as to be rotatable with respect to a rotating shaft 750.

The platform leg 720 can be rotatable between a first position and a second position. The platform leg 720 can be positioned in alignment with the platform body 710 in a first direction X at the first position. In addition, the platform leg 720 can be positioned in alignment with the platform body 710 in a second direction Y at the second position. The first direction X and the second direction Y can be perpendicular to each other.

The gantry 10 can be fixed at the moving platform 700 by the locking member 900. The gantry 10 and the moving platform 700 can be coupled to each other to be movable integrally by the locking member 900. At this time, the platform leg 720 of the moving platform 700 can be positioned at the second position. That is, the platform leg 720 can be foldable. For convenience, an assembly in which the gantry 10 is coupled with the moving platform 700 such that they can move integrally is referred to as "a moving module assembly". The moving module assembly can be movable by the casters 730 with the platform leg 720 folded. At this time, the casters 730 can be in contact with the floor while protruding from the platform body 710.

The moving module assembly can be fixed on the floor when arriving at a desired position in order to photograph an object. When the moving module assembly arrives at the desired position, the folded platform legs 720 can be unfolded, and the at least one supporting member 740 can contact the floor. That is, the platform leg 720 can be positioned at the first position. At this time, the casters 730 that provides mobility to the moving module assembly can be lifted inward of the platform body 710 to be spaced apart from the floor. When the platform leg 720 is unfolded in the first direction X, the first guide rail 810 and the second guide rail 820 can be spaced from each other, as shown in FIG. 18A. As shown in FIG. 18A, when the guide rail 800 exists discontinuously, it is difficult to expect a smooth movement of the moving module assembly. Therefore, as shown in FIG. 18B, the second guide rail 820 can be pressed and coupled with the first guide rail 810. When the first guide rail 810 and the second guide rail 820 are coupled to form one guide rail 800, a preparation process for moving the gantry 10 can be completed. When the locked state by the locking member 900 is released, the gantry 10 can move freely along the guide rail 800. The user can photograph the object while moving the gantry 10.

When the moving module assembly moves, the belt 1500 can be in a folded state, like the platform leg 720. When the moving module moves in order to photograph the object, the belt 1500 can be in an unfolded state, like the platform leg 720.

By implementing the movement of the gantry by using the guide rail and the moving member installed on the gantry, an influence of a state of a movement path on the movement of the gantry can be minimized, so that high-quality images of the object can be obtained.

It can be possible to more precisely and accurately control the movement of the gantry by using the guide rail and the belt together in a process of moving the gantry for photographing the object.

It is possible to improve a mobility of the gantry and ease of use of the medical device by designing the gantry in a configuration that is different from the table on which the object is positioned.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A medical device comprising:
   a gantry;
   a guide rail configured to guide a movement of the gantry when the gantry is moved;
   a belt retractably disposed in the gantry, and configured to be pulled out of the gantry to guide the movement of the gantry together with the guide rail; and
   a moving member disposed in the gantry to allow the gantry to move, and configured to be movable along the guide rail.

2. The medical device according to claim 1, wherein the belt is configured to be pulled out of the gantry in a path parallel to the guide rail.

3. The medical device according to claim 1, further comprising a belt holder coupled to one end of the belt and configured to facilitate withdrawal of the belt, the belt holder detachably mounted to the gantry.

4. The medical device according to claim 3, wherein the belt holder comprises a guide rail mounting portion to which the guide rail is detachably coupled.

5. The medical device according to claim 3, wherein the belt holder comprises:
   a belt holder body; and
   a belt winder rotatably positioned inside the belt holder body and configured to enable the belt to be wound.

6. The medical device according to claim 5, wherein the belt holder further comprises a belt winder driving unit positioned inside the belt holder body, the belt winder driving unit configured to rotate the belt winder using an elastic force.

7. The medical device according to claim 6, wherein the belt winder driving unit comprises an elastic member capable of being elastically deformed, and
   when the belt pulled out from the gantry, the belt is rewound by the belt winder by resilience of the elastic member.

8. The medical device according to claim 5, wherein the belt holder further comprises a belt clamp mounted on one side of the belt holder body facing the gantry so as to guide a movement of the belt.

9. The medical device according to claim 1, wherein the moving member comprises at least one chain.

10. The medical device according to claim 1, wherein the moving member comprises a slider movably coupled to the guide rail.

11. The medical device according to claim 1, further comprising:
    a caster mounted on the gantry, and configured to protrude from the gantry to enable the gantry to move.

12. The medical device according to claim 11, wherein the moving member and the caster selectively enable the gantry to move.

13. The medical device according to claim 1, further comprising:
    a moving member driving unit disposed inside the gantry to supply power to the moving member; and
    a first pulley unit disposed adjacent to the moving member driving unit, and configured to guide a movement of the belt inside the gantry, the first pulley unit comprising a plurality of idler pulleys and a drive pulley positioned above the plurality of idler pulleys in a height direction of the gantry.

14. The medical device according to claim 1, further comprising:
    a movement preventing unit disposed inside the gantry, and configured to prevent the moving member from moving; and
    a second pulley unit disposed adjacent to the movement preventing unit, and configured to guide a movement of the belt inside the gantry, the second pulley unit comprising a plurality of idler pulleys and a drive pulley positioned above the plurality of idler pulleys in a height direction of the gantry.

15. A medical device comprising:
    a gantry configured to photograph an object;
    a guide rail configured to guide a movement of the gantry when the object is photographed;
    a moving member disposed in the gantry, and configured to be movable along the guide rail when the object is photographed; and
    a caster retractably disposed in the gantry and spaced apart from the guide rail and moving member, and configured to enable a movement of the gantry when the object is not photographed.

16. The medical device according to claim 15, wherein the caster is configured to protrude from the gantry when the object is not photographed.

17. The medical device according to claim 15, further comprising:
    a belt disposed in the gantry, and capable of being pulled out of the gantry to guide the movement of the gantry together with the guide rail when the object is photographed.

18. The medical device according to claim 17, wherein the belt is positioned between the guide rail and the caster to be adjacent to the guide rail.

19. The medical device according to claim 17, wherein the belt comprises a toothed belt.

20. A medical device comprising:
    a gantry having a bore into which an object to be photographed is inserted;

a detachable guide rail detachably coupled to a belt holder and configured to guide a movement of the gantry when the gantry is moved;

a belt coupled to the belt holder and configured to be pulled out in an extending direction of the guide rail; and a moving member configured to be movable along the guide rail.

* * * * *